United States Patent
Bernard et al.

(10) Patent No.: US 9,869,681 B2
(45) Date of Patent: *Jan. 16, 2018

(54) PROCESS FOR TREATING AN INDIVIDUAL WITH AN ESTHETIC DEFECT OF SKIN BY MODULATING SASPASE FLG2 COMPLEX

(75) Inventors: Dominique Bernard, Vanves (FR); Agnes Thomas-Collignon, Montigny le Bretonneux (FR); Roger Rozot, Lagny sur Marne (FR); Benoit Muller, Paris (FR)

(73) Assignee: L'OREAL, Paris (FR)

( * ) Notice: Subject to any disclaimer, the term of this patent is extended or adjusted under 35 U.S.C. 154(b) by 684 days.

This patent is subject to a terminal disclaimer.

(21) Appl. No.: 13/992,589

(22) PCT Filed: Dec. 5, 2011

(86) PCT No.: PCT/IB2011/055455
§ 371 (c)(1),
(2), (4) Date: Sep. 16, 2013

(87) PCT Pub. No.: WO2012/077034
PCT Pub. Date: Jun. 14, 2012

(65) Prior Publication Data
US 2014/0005207 A1  Jan. 2, 2014

Related U.S. Application Data

(60) Provisional application No. 61/457,092, filed on Dec. 23, 2010.

(30) Foreign Application Priority Data

Dec. 7, 2010 (FR) ...................................... 10 60183

(51) Int. Cl.
*A61K 31/519* (2006.01)
*G01N 33/68* (2006.01)
*A61K 8/49* (2006.01)
*A61Q 19/00* (2006.01)
*A61Q 19/08* (2006.01)
*A61Q 15/00* (2006.01)

(52) U.S. Cl.
CPC ....... *G01N 33/6881* (2013.01); *A61K 8/4953* (2013.01); *A61K 31/519* (2013.01); *A61Q 19/007* (2013.01); *A61Q 19/08* (2013.01); *G01N 33/6845* (2013.01); *A61K 2800/78* (2013.01); *A61Q 15/00* (2013.01); *G01N 2500/02* (2013.01)

(58) Field of Classification Search
CPC .......... G01N 2500/02; G01N 33/6881; G01N 2333/96472; G01N 33/573; G01N 33/6845; A61K 8/64; A61K 2800/78; A61K 31/519; A61K 8/4953; A61Q 19/00; A61Q 15/00; A61Q 19/007; A61Q 19/08; C07K 14/47; C12N 9/06; C12N 9/6413

USPC ......... 435/188, 7.4; 514/18.8, 257; 530/324; 544/247
IPC ........ G01N 33/68,33/573; C07K 14/47; A61K 31/519, 8/60, 8/64; A61Q 19/00; C12N 9/64

See application file for complete search history.

(56) References Cited

U.S. PATENT DOCUMENTS

| | | | |
|---|---|---|---|
| 7,521,422 B2 | 4/2009 | Bernard et al. | |
| 9,464,080 B2 * | 10/2016 | Marat | A61K 8/4953 |
| 2009/0186821 A1 | 7/2009 | Bernard et al. | |
| 2010/0035867 A1 | 2/2010 | Guerrant et al. | |

FOREIGN PATENT DOCUMENTS

| FR | 2 842 209 | 1/2004 |
|---|---|---|
| WO | 2008 008704 | 1/2008 |

OTHER PUBLICATIONS

Copending U.S. Appl. No. 14/405,969, filed Dec. 5, 2014.*
Agarwal, A. et al., "Solid supported synthesis of structurally diverse dihydropyrido(2,3-d)pyrimidines using microwave irradiation", Tetrahedron Letters, ELSEVIER, vol. 46, No. 8, pp. 1345 to 1348, (2005), XP 004756250.
Matsui, T. et al., "Mouse Homologue of Skin-specific Retroviral-like Aspartic Protease Involved in Wrinkle Formation", Journal of Biological Chemistry, vol. 281, No. 37, pp. 27512 to 27525, (Sep. 15, 2006), XP-002561740.
Coffeen, W. et al., "Purification and Characterization of Serine Proteases That Exhibit Caspase-Like Activity and Are Associated with Programmed Cell Death in *Avena sativa*", The Plant Cell, vol. 16, pp. 857 to 873, (Apr. 2004), XP-002649085.
Wu, Z, et al. "Molecular Identification and Expresiion Analysis of Filaggrin-2, a Member of the S100 Fused-Type Protein Family", PLoS ONE, vol. 4, No. 4, pp. 1 to 13, (Apr. 2009).
French Search Report dated Jul. 15, 2011 in French Patent Application 1060183 Filed Dec. 7, 2010.
International Search Report dated Mar. 16, 2012 in PCT/IB11/55455 Filed Dec. 5, 2011.
U.S. Appl. No. 13/992,564, filed Jun. 7, 2013, Bernard, et al.

* cited by examiner

*Primary Examiner* — Pablo S Whaley
*Assistant Examiner* — Kailash C Srivastava
(74) *Attorney, Agent, or Firm* — Oblon, McClelland, Maier & Neustadt, L.L.P.

(57) ABSTRACT

The present invention relates to the use of a compound, suitable for modulating the interaction between first and second partner proteins, or between homologues, mutants, or fragments of said proteins, said first and second proteins being SASPase and filaggrin-2, or FLG2, as an active agent for treating and/or preventing aesthetic defects in the skin, and/or in the appendages thereof, linked to an imbalance in the differentiation and/or proliferation of the cells of the epidermis.

8 Claims, 1 Drawing Sheet

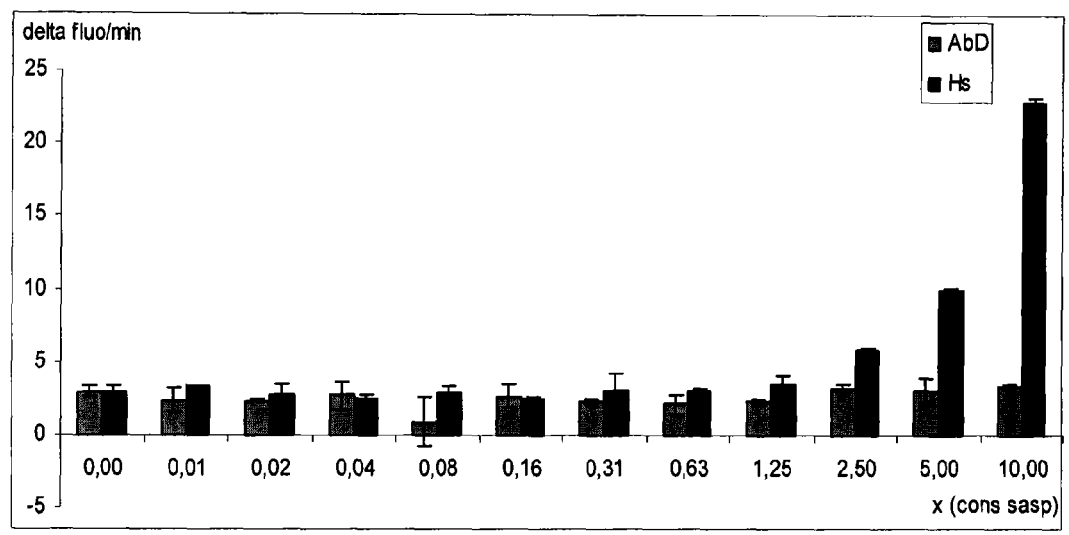

PROCESS FOR TREATING AN INDIVIDUAL WITH AN ESTHETIC DEFECT OF SKIN BY MODULATING SASPASE FLG2 COMPLEX

CONTINUING APPLICATION INFORMATION

The present application is a National Stage of International Application No. PCT/IB11/055455, filed on Dec. 5, 2011, which claims benefit of the filing date of Provisional Application Ser. No. 61/457,092, filed on Dec. 23, 2010.

The present invention relates to a novel cosmetic or therapeutic target that is useful with regard to the skin and its integuments, and also to its use for cosmetic, therapeutic or dermatological care purposes.

More precisely, the present invention relates to a novel protein complex involved in epidermal cell differentiation and/or proliferation, to its use as a tool for screening novel cosmetic or therapeutic active agents, to the novel active agents identified, and to the use thereof for preventing and/or treating esthetic defects or pathological disorders of the skin and/or its integuments.

The term "the skin" means the entire skin of the body, including the scalp and mucous membranes.

The term "skin integuments" means bodily hairs, the eyelashes, head hair and the nails.

The skin, or epidermis, is conventionally divided into a basal layer of keratinocytes that constitutes the germinal layer of the epidermis, a spinous layer consisting of several layers of polyhedral cells positioned on the germinal layer, one to three "granular" layers consisting of flattened cells containing distinct cytoplasmic inclusions, keratohyalin granules, and finally an assembly of upper layers known as the cornified layers, or stratum corneum, consisting of keratinocytes at the terminal stage of their differentiation, known as corneocytes.

Corneocytes are anuclear cells mainly consisting of a fibrous material containing cytokeratins, surrounded by a cornified envelope. New keratinocytes undergo permanent production to compensate for the continual loss of epidermal cells from the cornified layer by a mechanism known as desquamation. The process as a whole leading to the formation of the stratum corneum and to its removal is subject to a finely regulated equilibrium controlled by several hormonal or cellular factors. An imbalance in one of these factors, if not rapidly corrected, ends up being reflected by an imbalance between the production of basal layer cells and the rate of desquamation.

Many esthetic defects or pathological disorders of the skin or its integuments may be associated with an epidermal homeostasis defect and in particular a cell proliferation and/or differentiation defect.

Thus, when the cell proliferation and/or differentiation of the basal layer of the epidermis are accelerated relative to the rate of desquamation or when this rate is slowed down, the stratum corneum then has a tendency to become thickened. In the case of mild manifestations of this imbalance, it may appear in the form of various esthetic defects of the skin or its integuments, for instance signs of aging of the skin, skin barrier function defects, signs of skin dryness or signs of cutaneous hyperseborrhea. On the other hand, the aggravated manifestations of this imbalance may appear in the form of various pathological disorders, for instance hyperkeratosis, xerosis, ichthyosis, psoriasis, certain benign or malignant tumoral lesions, or rectional hyperkeratosis.

Conversely, a slowing-down of the cell proliferation and/or differentiation of the basal layer relative to desquamation, or an acceleration of desquamation, may be manifested by thinning of the epidermis, and more particularly of the cornified layer. The mild manifestations of this imbalance may be expressed by excessive fragility of the cutaneous covering, or even by various esthetic defects of the skin or its integuments, such as a cicatrization defect, or a re-epithelialization defect, especially after a cutaneous scrubbing or exfoliant treatment. The aggravated manifestations of this imbalance may appear in the form of various pathological disorders, for instance reactions of immune origin, generally induced by contact of the skin with one or more exogenous agents.

Many aspects of the mechanisms underlying the regulation of the equilibrium between the proliferation and differentiation of the epidermal cells remain to be determined.

Thus, the identification and determination at the cellular and molecular level of the mechanisms involved in the formation of the stratum corneum would make it possible to provide novel targets that are useful with regard to cosmetic or therapeutic care of the skin and/or its integuments.

There is thus still a need for novel molecular targets involved in the formation of the stratum corneum, and especially in the proliferation and/or differentiation of epidermal cells.

There is also a need for novel cosmetic and/or therapeutic targets involved in the metabolic and/or signaling routes underlying the proliferation and/or differentiation of epidermal cells.

There is also a need for novel tools for screening active compounds that are capable of modulating the proliferation and/or differentiation of epidermal cells.

There is also a need for novel active compounds that are capable of modifying, correcting, restoring and/or reinforcing the physiological functions of the epidermis.

There is also a need for novel active compounds that are capable of exerting a cosmetic or therapeutic care effect with regard to the skin or its integuments.

There is also a need for novel active compounds that are capable of preventing and/or treating an esthetic defect or a pathological disorder of the skin or its integuments, resulting from an epidermal cell proliferation and/or differentiation defect.

The object of the present invention is to satisfy these needs.

Thus, the present invention relates to a cosmetic use of at least one compound that is capable of modulating the interaction between a first and a second partner protein, homologs, mutants or fragments of said proteins, said first and second proteins being SASPase and filaggrin-2, or FLG2, as an active agent for treating and/or preventing an esthetic defect of the skin and/or its integuments associated with an imbalance in epidermal cell differentiation and/or proliferation.

Hereinbelow, the terms "protein" and "protein sequence" are used equivalently and indiscriminantly, unless otherwise mentioned, to denote a protein, a homolog, a mutant or a fragment thereof.

For the purposes of the invention, the term "modulating" means promoting, reducing or stabilizing the interaction between proteins.

The inventors have demonstrated, unexpectedly, firstly, the manifestation of an interaction between the aspartic acid protease SASPase and the protein filaggrin-2 or FLG2, more particularly via the N-terminal part corresponding to part S100 of this protein, in the epidermis, and, secondly, that this interaction promotes the proteolytic activity of SASPase.

FR 2 842 209 teaches that the protein SASPase is strongly expressed in the epidermis, and is involved in skin desquamation processes, and describes this protein as a target in the treatment of skin disorders. However, said document does not mention the SASPase-FLG2 interaction or the involvement of this protein complex in regulating epidermal cell differentiation or proliferation.

In addition, the inventors have shown that the SASPase-FLG2 interaction can be modulated by means of various active compounds, and that this modulation could be useful for preventing and/or treating an esthetic defect or a pathological disorder of the skin and/or its integuments, following an imbalance in epidermal cell differentiation and/or proliferation.

For the purposes of the invention, the term "regulating epidermal cell proliferation and/or differentiation" means re-establishing a physiological equilibrium between these two processes.

For the purposes of the present invention, the term "preventing" means reducing the risk or probability of manifestation of a given phenomenon, i.e., in the present invention, an esthetic defect or a pathological disorder of the skin and/or its integuments associated with an imbalance in epidermal cell differentiation and/or proliferation.

According to another aspect, the present invention relates to the cosmetic use of at least one compound as defined previously, as an active agent for promoting re-epithelialization after a cutaneous scrubbing or exfoliant treatment.

According to yet another aspect, the present invention relates to the cosmetic use of at least one compound as defined above, as an active agent for preventing and/or treating hair loss and/or promoting hair regrowth, or for preventing bodily hair regrowth.

According to another embodiment, the present invention relates to the use of at least one protein complex comprising a first and a second partner protein interacting with each other, said first and second proteins being SASPase and filaggrin-2, or FLG2, homologs, mutants or fragments of said proteins, for screening compounds that are capable of regulating the homeostasis of an epidermis, and in particular the proliferation and/or differentiation of epidermal cells by modulating the interaction between said first and second proteins.

For the purposes of the invention, the term "regulating epidermal cell proliferation and/or differentiation" means re-establishing a physiological equilibrium between these two processes.

According to another embodiment, the present invention relates to a process for screening a compound that is capable of regulating the homeostasis of an epidermis, and in particular the proliferation and/or differentiation of epidermal cells by modulating the interaction between a first and a second partner protein, homologs, mutants or fragments of said proteins, said first and second proteins being SASPase and filaggrin-2, or FLG2, said process comprising at least the steps described below.

Preferably, a process or a use of the invention may be performed in vitro, ex vivo or in vivo, and more preferably in vitro or ex vivo.

According to another embodiment, the present invention relates to a pharmaceutical or dermatological composition comprising, in a physiologically acceptable medium, at least an effective amount of at least one compound of the invention, for preventing and/or treating a pathological disorder of the skin and/or its integuments associated with an imbalance in epidermal cell differentiation and/or proliferation.

According to another embodiment, the present invention relates to a cosmetic composition comprising, as active agent, in a physiologically acceptable medium, at least an effective amount of at least one compound of the invention, and at least one cosmetically or dermatologically acceptable ingredient chosen from cosmetic or dermatological active agents, preserving agents, hydrophilic or lipophilic gellants, nonionic, anionic or cationic surfactants, antioxidants, salts, fragrances, fillers, odor absorbers, dyestuffs, film-forming polymers, semicrystalline polymers, gums and volatile or nonvolatile oils, and mixtures thereof.

For the purposes of the present invention, the term "physiologically acceptable medium" means a medium that is compatible with administration to an individual, especially onto or into the skin and/or its integuments of this individual.

For the purposes of the present invention, the term "effective amount" of a compound of the invention means an amount of this compound that is sufficient and necessary to exert a preventive and/or treating effect with regard to an esthetic defect or a pathological disorder of the skin and/or its integuments. Such an amount can be determined by any method known to a person skilled in the art, for example by means of in vitro, ex vivo or in vivo trials, such as clinical trials.

According to yet another aspect, the present invention relates to an article for conditioning a cosmetic, pharmaceutical or dermatological composition, containing at least one cosmetic, pharmaceutical or dermatological composition comprising at least one compound of the invention.

According to another embodiment, the present invention relates to a cosmetic process for preventing and/or treating an esthetic defect of the skin and/or its integuments associated with an imbalance in epidermal cell differentiation and/or proliferation in an individual, comprising at least one step of administering to said individual at least one compound of the invention.

According to another embodiment, the present invention relates to a protein complex comprising a first and a second partner protein that interact with each other, said first and second proteins being SASPase and filaggrin-2, or FLG2, homologs, mutants or fragments of said proteins.

The present invention advantageously affords a novel target that may be used in cosmetics or in therapeutics with regard to the skin and/or its integuments, especially with respect to the skin.

Also advantageously, the present invention provides a novel screening tool that is particularly effective and sensitive for the detection of novel active agents that are useful in cosmetics or in therapeutics with regard to the skin and/or its integuments.

The present invention advantageously provides novel active agents that are useful in cosmetics or in therapeutics, and which are capable of regulating the homeostasis of an epidermis, and in particular epidermal cell proliferation and/or differentiation, and which in particular have good efficacy and good tolerance.

The present invention advantageously affords novel cosmetic or therapeutic compositions that are particularly effective with regard to esthetic defects or pathological disorders of the skin and/or its integuments associated with an imbalance in epidermal cell proliferation and/or differentiation.

Finally, the present invention advantageously affords a novel cosmetic treatment or prevention process that is particularly effective with regard to esthetic defects of the skin and/or its integuments associated with an imbalance in epidermal cell proliferation and/or differentiation.

SASPase-FLG2 Complex

As indicated previously, the invention relates to a protein complex resulting from the interaction between two proteins, SASPase and FLG2, and to the use of this complex as a biological marker and target of epidermal cell differentiation and/or proliferation.

A complex of the invention may be formed by interaction of all or part of a first protein sequence of SASPase with all or part of a second protein sequence of FLG2 or a dimer of this second sequence.

SASPase, or Skin Aspartic Protease, is a protein of the "aspartic acid" protease family, comprising 343 amino acids (Uniprot/Swissprot: Q53RT3) and having a molecular weight of about 37 kDa.

Its short form comprises 259 amino acids, for a molecular weight of about 28 kDa, and is represented by a sequence extending from position 85 to position 343 of the sequence Q53RT3 (Uniprot/Swissprot reference). Preferably, a protein sequence of SASPase that is useful for the invention is represented by the sequence extending from position 85 to position 343 of the sequence Q53RT3.

Filaggrin-2, or FLG2, is a 2391-amino acid protein with a molecular weight of about 248 kDa (Uniprot/Swissprot ref.: Q5D862).

FLG2 is a protein of "fused-type" S100, whose structure is similar to that of filaggrin, which is expressed in the epidermis, and which is presented as being capable of being involved in epidermal cell differentiation, the formation of the epidermal barrier, protection of the skin against environmental attack, the organization of the network of intermediate keratin filaments giving the epidermis its strength, and also in skin moisturization (Wu et al., PLoS One, 2009; 4(4):e5227).

According to one embodiment, the FLG2 used according to the invention may be represented by an amino acid sequence extending from positions 2 to 213 of the sequence Q5D862, and more preferentially from positions 2 to 95, or a dimer of these sequences.

The use of the invention also extends to the nucleic acid sequences coding for the proteins, homologs, mutants and fragments of the proteins that are suitable for use in the invention.

The expression "homolog" of a protein sequence or a nucleic acid sequence denotes having an identity of at least 85%, in particular of at least 90%, in particular of at least 98%, and more particularly of at least 99%, with said sequence, and having biological activity of the same nature.

Sequence homology may be identified by any technique usually used in the field by a person skilled in the art. By way of example, sequence homology may be determined by using the BLAST computer interface available on the NCBI web site at the address http://blast.ncbi.nlm.nih.gov, configured with the default parameters.

A homolog of a protein sequence may differ from this sequence, for example, by one or more deletion(s) and/or insertion(s) and/or one or more substitution(s) of an amino acid. Similarly, a homolog of a nucleic acid sequence may differ from this sequence, for example, by one or more deletion(s) and/or insertion(s) and/or one or more substitution(s) of a base or of a codon. These modifications may be combined.

According to one embodiment variant, a homolog of a protein or nucleic acid sequence may comprise one or more conservative substitutions of amino acids or of codons.

A conservative substitution is the replacement, in a protein sequence, of one amino acid with another amino acid that has substantially similar, or sufficiently close, physicochemical properties to those of the original amino acid, for the properties and functions of the protein to be unaffected, or not substantially affected. Similarly, a conservative substitution is a replacement, in a nucleic acid sequence, of one codon with another codon coding for an identical amino acid or an amino acid that has substantially similar, or sufficiently close, physicochemical properties to those of the original amino acid, for the properties and functions of the coded nucleic acid sequence to be unaffected, or not substantially affected.

The modifications of the protein or nucleic acid sequences presented above may be referred to in general as "mutations". Thus, the homologs of the invention also concern the mutants and variants of the amino acid or nucleic acid sequences of the invention.

As examples of mutations that may be considered in the present invention, mention may be made of the replacement of one or more amino acid residues with amino acid residues having a similar hydropathic index, without, however, substantially affecting the biological properties of the protein, and especially its property of interaction with its partner protein. The hydropathic index is an index assigned to amino acids according to their hydrophobicity and their charge (Kyte and Doolittle (1982), J. Mol. Biol., 157: 105).

A protein of the invention may comprise one or more post-translational modification(s).

The term "post-translational modification(s)" is intended to encompass all the modifications that a peptide or protein is liable to undergo at the end of its synthesis in a cell, for instance one or more phosphorylation(s), one or more glycosylation(s), one or more citrullination(s), one or more lipidation(s), such as a farnesylation or a palmitoylation, a structural rearrangement such as disulfide bridge formation and/or cleavage within the protein sequence.

Sequence homology may be assessed with regard to the entire sequence of the protein or to one or more characteristic sequences of this protein.

The term "characteristic sequence" of a protein means an amino acid sequence that is determinant in the identity of the protein and involved in its biological activity, for instance the maintenance of its three-dimensional structure, its affinity with the cell elements with which the protein usually interacts, such as other proteins, nucleic acid sequences, sugars or lipids, its enzymatic activity or its activity as a substrate with regard to other enzymes.

More particularly, characteristic sequences of SASPase or of FLG2 that are suitable for use in the invention are sequences involved in the interaction of these proteins with each other.

According to one embodiment, the characteristic sequences that are more particularly under consideration may be the N-terminal sequences of the proteins SASPase and FLG2.

According to a particular embodiment variant, a characteristic sequence of SASPase that is suitable for use in the invention may be included in the N-terminal part of SASPase, short form, and may more particularly be a sequence extending from position 97 to position 173 of the sequence Q53RT3 (Uniprot/Swissprot reference).

According to another embodiment variant, a characteristic sequence of FLG2 that is suitable for use in the invention may be included in the N-terminal part of FLG2, and more particularly may be a sequence extending from position 2 to position 95 of the sequence Q5D862 (Uniprot/Swissprot reference).

Preferably, the characteristic sequences of SASPase and/or FLG2 may advantageously be used in the invention.

The term "biological activity of the same nature" of a protein of the invention means its capacity to interact with the second partner protein of the invention. The term "biological activity of the same nature" of a nucleic acid sequence in particular means its capacity to be transcribed and translated into an amino acid sequence.

With regard to SASPase, a biological activity of the same nature may also mean its proteolytic activity, especially with regard to corneodesmosin.

The invention also relates to the use of SASPase mutants which may comprise one or more mutations in the active site responsible for its hydrolytic activity. In particular, the mutations under consideration in the invention may lead to a reduction or elimination of the proteolytic activity of SASPase. In this embodiment, a biological activity of the same nature with regard to SASPase may then mean its property of interaction of the inactive mutant of SASPase with FLG2, a mutant, a homolog or a fragment thereof.

As an example of a mutant recombinant SASPase protein that is suitable for use in the invention, mention may be made of the protein comprising the mutation consisting of the replacement of the aspartic acid in position 212 of the sequence Q53RT3 (Uniprot/Swissprot reference) with an alanine (D212A). This mutation is equivalent, in the 28-kDa form of SASPase, to the mutation D128A. A mutant protein of SASPase may be obtained via any molecular biology process known to those skilled in the art.

With regard to FLG2, a biological activity of the same nature may also mean its property of interacting with SASPase and/or of promoting and increasing the proteolytic activity of SASPase.

According to another variant of the invention, a biological activity of the same nature may also mean the biological activity of a complex of the invention with regard to the proliferation and/or differentiation of epidermal cells.

According to another embodiment variant of the invention, during the use of at least one inactive mutant of one of the two partner proteins of a complex of the invention, the term "biological activity of the same nature" means the property of the partner proteins to interact together and to form a complex.

Thus, a mutant, a homolog or a fragment of the first and second partner proteins that are suitable for use in the invention necessarily have at least the property of interacting with each other to form a complex that is suitable for use in the invention.

For the purposes of the invention, the term "fragment of a protein" means any portion of a protein in accordance with the invention comprising from 6 to 260 amino acids, preferably from 3 to 215 amino acids, preferably from 10 to 180 amino acids, and more preferably from 20 to 140, or even from 40 to 100, or from 60 to 100 contiguous amino acids, and having biological activity of the same nature as that expressed by the protein.

The term "fragment" with regard to a nucleic acid sequence denotes any portion of this sequence, consisting of from 18 to 780 bases, preferably from 24 to 645 bases, preferably from 30 to 540 bases and even more preferably from 6 to 420 bases, or even from 120 to 300 or from 180 to 300 bases, and coding for a fragment of the amino acid sequence encoded by said sequence.

Preferably, a fragment of the invention is derived from the N-terminal part of a protein of the invention.

According to one embodiment variant, a SASPase protein that is suitable for use in the invention may comprise only an amino acid sequence extending from position 95 to 160 of the SASPase protein (Uniprot/Swissprot reference: Q53RT3).

Such a sequence conserves the property of interaction of SASPase with FLG2, but is devoid of proteolytic activity.

According to another embodiment, the FLG2 used according to the invention may consist of the first 100 N-terminal amino acids, or even the first 95 N-terminal amino acids, and may preferentially consist of an amino acid sequence extending from positions 2 to 95 of the sequence Q5D862 (Uniprot/Swissprot).

According to one embodiment, a protein that is suitable for use in the invention may be a natural or synthetic protein, which may be obtained, where appropriate, by chemical or biological synthesis, or by extraction from a biological tissue, for instance the skin, which expresses a protein naturally or after translation, and also the various post-translational forms thereof, and also the homologs, mutants or fragments thereof.

According to another embodiment, the invention relates to a chimeric protein comprising a first protein sequence fused or coupled with a second protein sequence, a hydrophilic or hydrophobic targeting agent, a bioconversion precursor, an affinity marker, for example a fluorescent marker, a luminescent marker, a radioactive marker or a colorimetric marker.

In a nonlimiting manner, mention may be made, as examples of compounds that may be coupled with a protein in accordance with the invention, of fluorescent proteins such as Green Fluorescent Protein, fluorescent chemical compounds, such as rhodamine, fluorescein, or Texas Red, phosphorescent compounds, radioactive elements, such as $^3$H, $^{35}$S, $^{121}$I or $^{125}$I, or colorimetric markers such as chromogenic substrates sensitive to the action of galactosidase, of peroxidase, of chloramphenicol acetyltransferase, of luciferase or of alkaline phosphatase, or alternatively affinity markers.

According to a preferred embodiment, a protein according to the invention may be coupled with an affinity marker, chosen in particular from a marker Myc, FLAF, His, His-tag, GST (glutathione S-transferase), THX (thioredoxin), MBP (maltose-binding protein), THX-His-tag or THX-His-S-tag.

According to the nature of the compounds that may be coupled with a protein in accordance with the invention, the coupling may be performed via any chemical process or via any molecular biology process known to those skilled in the art. In the latter case, it may be referred to as a fusion protein or a chimeric protein.

Thus, according to one embodiment, a SASPase protein that is suitable for use in the invention may in particular be a recombinant protein fused with an affinity marker.

According to one embodiment, a recombinant FLG2 protein that is suitable for use in the invention may be a recombinant protein fused with an affinity marker.

A recombinant protein of the invention, in mutated or nonmutated form, and in truncated or nontruncated form, where appropriate fused with another protein, for example an affinity marker, may be obtained via any molecular biology process, especially as described by Sambrook et al. (Molecular Cloning: A laboratory Manual, Ed. Cold Spring Harbor, 2001).

The use of the invention also extends to the nucleic acid sequences coding for the proteins, homologs, mutants and fragments of the proteins that are suitable for use in the invention.

A nucleic acid sequence coding for the SASPase protein, which is suitable for use in the invention, may be, for example, the nucleic acid sequence identified under the GenBank reference AK055994, AK057813, BC031997, BC094000 or BC094002, and preferably under the GenBank reference AK055994.

A nucleic acid sequence coding for an FLG2 protein, which is suitable for use in the invention, may be, for example, the nucleic acid sequence identified under the GenBank reference AY827490.1.

A nucleic acid sequence that is suitable for use in the invention may be used in particular for the preparation of any protein in accordance with the invention, and more particularly for the preparation of proteins fused to an affinity marker.

A nucleic acid sequence that is suitable for use in the invention may be of any possible origin, namely animal, in particular mammalian and even more particularly human, or plant, or from microorganisms, for instance viruses, phages or bacteria, or else from fungi, without any preconception as to whether or not it is naturally present in said organism.

Modulatory Compounds

For the purposes of the invention, the term "modulatory compound" means any compound that is capable of acting directly on a protein complex of the invention in order to modulate the interaction between the partner proteins of this complex.

For the purposes of the invention, the term "modulating" means promoting, reducing or stabilizing the interaction between these proteins.

A modulatory compound of the invention may bind to one or both of the partner proteins. This binding may take place, for example, on the protein domain(s) involved in the interaction. Thus, a modulatory compound of the invention may interact more particularly with a domain of the N-terminal part of the short form of SASPase, or of the N-terminal part of FLG2. Alternatively, a modulatory compound may bind simultaneously to the domain of the protein sequences of SASPase and of FLG2 involved in the formation of complexes.

Alternatively, this binding may take place remotely from the site of interaction of the proteins, leading allosterically to a conformational change in one or both of the proteins, and to a modulation of the interaction between the two proteins, or the function of these proteins.

Depending on the modulatory compound under consideration, the interaction between SASPase and FLG2 may be reinforced, reduced, eliminated or stabilized.

According to one embodiment, a modulatory compound may promote or be an agonist of the SASPase-FLG2 interaction. Alternatively, a modulatory compound may be a compound that destabilizes or antagonizes the SASPase-FLG2 interaction.

The agonist or antagonist nature of a compound which modulates the SASPase-FLG2 interaction will be retained according to the modulatory effect to be exerted on epidermal cell proliferation and/or differentiation, and more particularly according to the nature of the esthetic defect or pathological disorder of the skin or its integuments that is to be prevented or treated.

More particularly, in the context of esthetic defects or pathological disorders associated with an insufficiency of desquamation or an acceleration of epidermal cell proliferation and/or differentiation, a modulatory compound which is an agonist of or which promotes the SASPase-FLG2 interaction may be preferred.

Such a compound may exert pro-desquamating and/or antiaging activity on epidermal cells, thus promoting thickening of the live epidermis and regulating the thickness of the stratum corneum.

Alternatively, with regard to esthetic defects or pathological disorders of the skin and/or its integuments resulting from excessive desquamation or from an insufficiency of epidermal cell proliferation and/or differentiation, a modulatory compound which antagonizes or destabilizes the SASPase-FLG2 interaction may advantageously be used.

Such a compound may exert pro-differentiating activity on the epidermal cells, promoting maturation of the barrier function.

According to one embodiment, a compound that is more particularly under consideration according to the invention may be represented by the general formula (Ia) or (Ib) below:

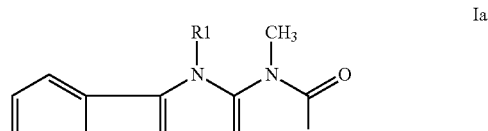

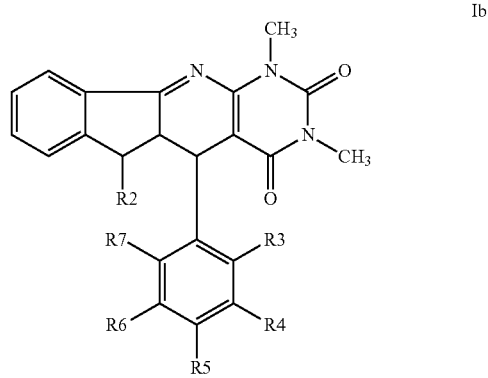

in which:
R$^1$ represents H, a linear or branched, saturated or unsaturated C$_1$-C$_4$ alkyl, or —C(O)R$^8$, in which R$^8$ represents a linear or branched, saturated or unsaturated C$_1$-C$_4$ alkyl;

R$^2$ represents =O, —OR$^9$ or —OC(O)R$^9$, in which R$^9$ represents H or a C$_1$-C$_2$ alkyl;

R$^3$, R$^4$, R$^5$, R$^6$ and R$^7$ represent, independently of each other, H; —NO$_2$; —OH; a fluorine; —CF$_3$; a linear or branched, saturated or unsaturated C$_1$-C$_4$ alkyl; a phenyl; —OC(O)—CH(Ph)$_2$; —O-Ph-X with X representing H, —OH, —NO$_2$, a fluorine, a linear or branched, saturated or unsaturated C$_1$-C$_4$ alkyl or alkoxy; —O—S(O$_2$)-Ph-Z with Z representing a linear or branched, saturated or unsaturated C$_1$-C$_4$ alkyl; —R$^8$OH; —OR$^9$; —OC(O)R$^9$ with R$^8$ and R$^9$ being as defined previously; —R$^{10}$Ph with R$^{10}$ being a linear or branched, saturated or unsaturated C$_1$-C$_4$ alkylene; or —OC(O)—Y$_n$—Ar$_1$—(X)$_m$ with n being 0 or 1 and m being an integer ranging from 0 to 4, with the proviso that n and m are not simultaneously 0, Y representing a linear or branched, saturated or unsaturated C$_1$-C$_4$ alkylene, X being as defined previously, and Ar$_1$ being

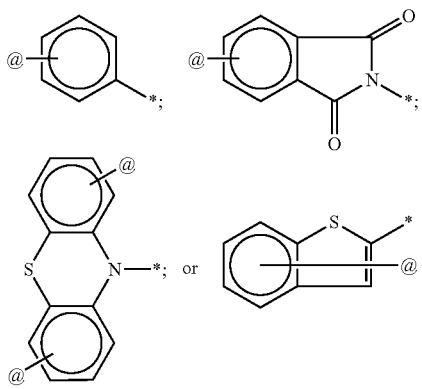

with * being a bond with Y and @ is a bond with X and physiologically acceptable salts thereof.

$R^1$ may especially represent H, a linear or branched, saturated or unsaturated $C_1$-$C_3$ alkyl, or —C(O)$R^8$ in which $R^8$ represents a linear or branched, saturated or unsaturated $C_1$-$C_3$ alkyl.

Preferably, $R^1$ may represent H, a methyl, an ethyl or a propyl, or —C(O)$R^8$ in which $R^8$ represents a methyl, an ethyl or a propyl.

Even more preferably, $R^1$ may represent a methyl, an ethyl or a propyl, and preferably H.

In particular, a compound of the invention may be represented by formula (Ia) in which $R^1$ represents H, a methyl, an ethyl or a propyl, and preferably represents H.

$R^2$ may represent =O or —O$R^9$, $R^9$ being as defined previously.

Advantageously, $R^2$ may represent =O or —O$R^9$ in which $R^9$ represents H or a methyl.

Preferably, $R^2$ may represent =O.

According to one embodiment, $R^3$, $R^4$, $R^5$, $R^6$ and $R^7$ may represent, independently of each other, H; —OH; a fluorine; a linear or branched, saturated or unsaturated $C_1$-$C_3$ alkyl; a phenyl; —OC(O)—CH(Ph)$_2$; —O-Ph-X with X representing H, —OH, —NO$_2$, a fluorine, a linear or branched, saturated or unsaturated $C_1$-$C_3$ alkyl or alkoxy; —O—S(O$_2$)-Ph-Z with Z representing a linear or branched, saturated or unsaturated $C_1$-$C_3$ alkyl; —$R^8$OH; —O$R^9$; —OC(O)$R^9$ with $R^8$ representing a linear or branched, saturated or unsaturated $C_1$-$C_3$ alkyl, and $R^9$ representing H or a methyl; —$R^{10}$Ph with $R^{10}$ being a linear or branched, saturated or unsaturated $C_1$-$C_3$ alkylene; or —OC(O)—Y$_n$—Ar$_1$—(X)$_m$ with n being 0 or 1 and m being an integer ranging from 0 to 4, Y representing a linear or branched, saturated or unsaturated $C_1$-$C_3$ alkylene, X representing H, —OH, a fluorine, a linear or branched, saturated or unsaturated $C_1$-$C_3$ alkyl or alkoxy, Ar$_1$ being:

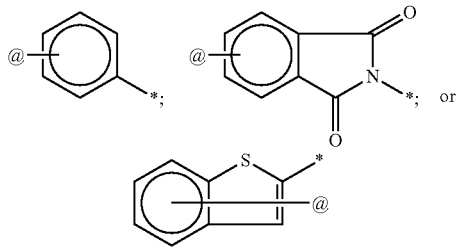

with * being a bond with Y and @ is a bond with X.

According to one embodiment, $R^3$, $R^4$, $R^5$, $R^6$ and $R^7$ may represent, independently of each other, H; —OH; a fluorine; a methyl or an ethyl; a phenyl; —OC(O)—CH(Ph)$_2$; —O-Ph-X with X representing H, —OH, a fluorine, a methyl, an ethyl, a methoxy or an ethoxy; —O—S(O$_2$)-Ph-Z with Z representing a methyl or an ethyl; —$R^8$OH; —O$R^9$; —OC(O)$R^9$ with $R^8$ representing a methyl or an ethyl and $R^9$ representing H or a methyl; —$R^{10}$Ph with $R^{10}$ being a methylene or an ethylene, or —OC(O)—Y$_n$—Ar$_1$—(X)$_m$ with n, Y, X and Ar$_1$ being as defined previously.

According to one embodiment, $R^3$, $R^4$, $R^5$, $R^6$ and $R^7$ may represent, independently of each other, H; —OH; a fluorine; a methyl or an ethyl; —$R^8$OH with $R^8$ representing a methyl or an ethyl; —O$R^9$ with $R^9$ representing H or a methyl; or —OC(O)—Y$_n$Ar$_1$—(X)$_n$ with n, Y, X and Ar$_1$ being as defined previously.

According to one embodiment, one from among $R^3$, $R^4$, $R^5$, $R^6$ and $R^7$ may represent —OC(O)—Yn-Ar$_1$—X)$_m$ with n being 0 or 1 and m being an integer ranging from 0 to 3, and especially from 1 to 2, Y representing a linear or branched, saturated or unsaturated $C_1$-$C_3$ alkylene, and especially a methylene or an ethylene, X may represent H, —OH, a methyl, an ethyl, a methoxy or an ethoxy, especially H, a methyl or a methoxy, and preferably an ethyl or an ethoxy, and Ar$_1$ being:

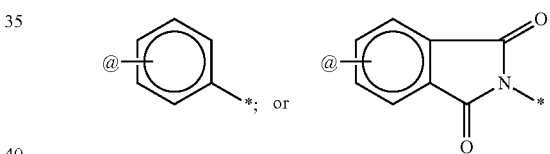

According to a preferred embodiment, in the group —OC(O)—Y$_n$—Ar$_1$—X$_m$, Ar$_1$ may be:

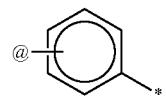

in which * and @ are as defined previously.

According to another preferred embodiment, in the group —OC(O)—Y$_n$—Ar$_1$—X$_m$, Y may be chosen from a methylene, an ethylene, a propylene, an isopropylene, and more preferentially may be chosen from a methylene and an isopropylene.

According to another preferred embodiment, in the group —OC(O)—Y$_n$—Ar$_1$—X$_m$, n may be equal to 0 and m may be equal to 1.

According to another preferred embodiment, in the group —OC(O)—Y$_n$—Ar$_1$—X$_m$, X may be chosen from a linear or branched, saturated or unsaturated $C_1$-$C_4$ and preferably $C_2$-$C_3$ alkyl or alkoxy. Preferably, X may be chosen from a methyl, an ethyl, a methoxy or an ethoxy. Even more preferentially, X may be a methyl or a methoxy, and preferably a methyl.

According to a preferred embodiment, in the group —OC(O)—$Y_n$—$Ar_1$—$X_m$, n may be equal to 0, m may be equal to 1, X may be a methyl or a methoxy, preferably a methyl, and $Ar_1$ may be:

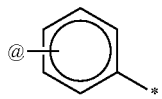

in which * and @ are as defined previously.

According to one embodiment, not more than one from among $R^3$, $R^4$, $R^5$, $R^6$ and $R^7$ may represent —OC(O)—$Y_n$—$Ar_1$—$X_m$, as defined previously, and preferably $R^4$ or $R^6$ represents —OC(O)—$Y_n$—$Ar_1$—$X_m$ as defined previously. According to one variant of this embodiment, —OC(O)—$Y_n$—$Ar_1$—$X_m$ may be such that n may be equal to 0, m equal to 1, X as defined previously, and $Ar_1$ may represent

with * being a bond with Y and @ is a bond with X.

According to one embodiment, $R^3$, $R^5$, $R^7$ and $R^4$ or $R^6$ may represent, independently of each other, H; —$NO_2$; —OH; a fluorine; a methyl or an ethyl; a phenyl; —$R^8$OH; —$OR^9$; —OC(O)$R^9$ with $R^8$ representing a methyl or an ethyl and $R^9$ representing H or a methyl; —$R^{10}$Ph with $R^{10}$ being a methylene or an ethylene.

According to a preferred embodiment variant, $R^3$, $R^5$, $R^7$ and $R^4$ or $R^6$ may represent, independently of each other, H, —OH, a fluorine, a methyl, and preferably represent H.

According to one embodiment, a compound of the invention may be represented in particular by the general formula (Ia).

According to a preferred mode of the invention, a compound that is suitable for use in the invention may preferably be represented by the compound of formula (II) below:

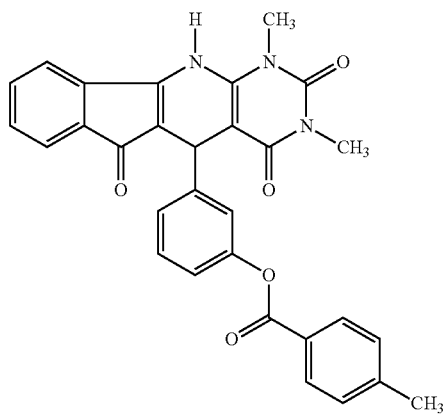

This compound is referred to hereinbelow as "M7".

A physiologically acceptable salt of a compound of general formula (Ia) or (Ib) according to the invention may be a salt of a compound of general formula (Ia) or (Ib) and of an alkali metal, of an alkaline-earth metal or of ammonium, comprising the salts obtained with organic ammonium bases, or salts of a compound of general formula (Ia) or (Ib) and of an organic or mineral acid.

Salts that are more particularly suitable for use in the invention may be sodium, potassium, calcium or magnesium salts, quaternary ammonium salts such as tetramethylammonium or tetraethylammonium, and addition salts with ammonia and physiologically acceptable organic amines, such as methylamine, dimethylamine, trimethylamine, ethylamine, triethylamine, ethanolamine or tris(2-hydroxyethyl)amine.

Salts of a compound of general formula (Ia) or (Ib) and of a mineral acid that are suitable for use in the invention may be obtained with hydrochloric acid, hydrobromic acid, sulfuric acid, nitric acid or phosphoric acid.

Salts of a compound of general formula (Ia) or (Ib) and of an organic acid that are suitable for use in the invention may be obtained with carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid, benzenesulfonic acid or p-toluenesulfonic acid.

The modulatory compounds that are suitable for use in the invention may especially be obtained as described in patent application WO 2008/008 704.

Alternatively, the modulatory compounds that are suitable for use in the invention may be obtained from the databank ChemDiv Discovery Chemistry Collection Public Database (Order Number: 4477-2039), ChemDiv, Inc. San Diego, USA).

The modulatory compounds that are suitable for use in the invention may especially be obtained as described in Tetrahedron Letters, 2005, 46(8):1345-1348, according to the following schematic processes:

Solid Phase Synthesis

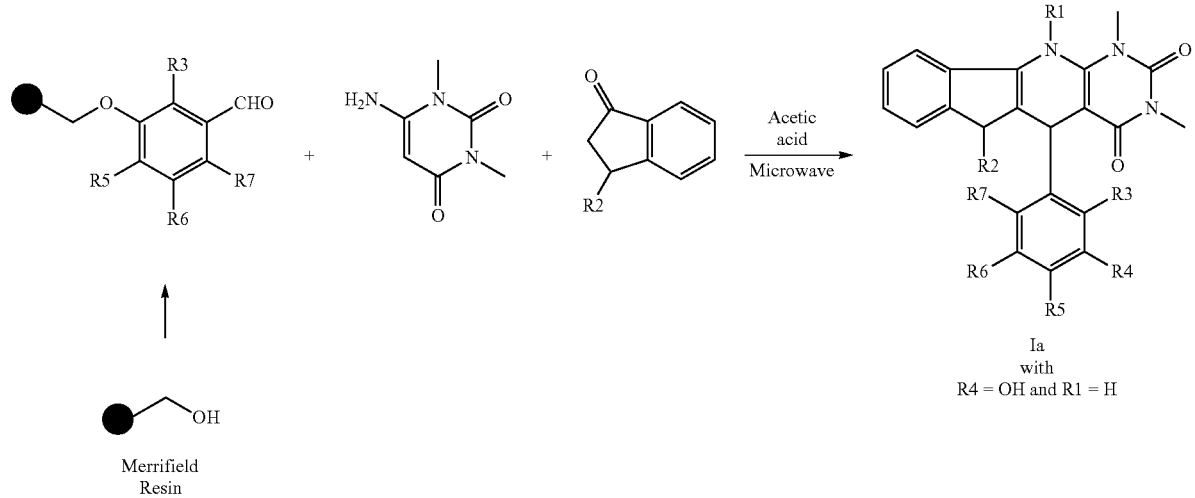

Liquid Phase Synthesis

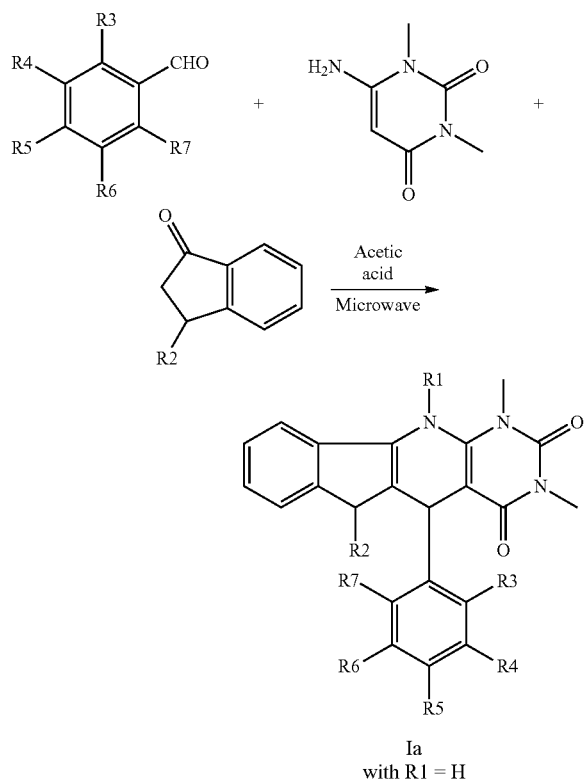

in which $R^1$, $R^2$, $R^3$, $R^4$, $R^5$, $R^6$ and $R^7$ may preferably be as defined above.

Screening

The invention relates to the use of a protein complex of the invention for screening novel compounds, in particular as defined previously.

According to one embodiment, the invention relates to a process for screening a compound that is capable of regulating the homeostasis of an epidermis, and in particular the proliferation and/or differentiation of epidermal cells by modulating the interaction between a first and a second partner protein, homologs, mutants or fragments of said proteins, said first and second proteins being SASPase and filaggrin-2, or FLG2, said process comprising at least the steps consisting in:

a) placing said first and second proteins under conditions suitable for interaction between the first and second proteins, b) combining, before or after step a), at least one of the first and second proteins with a species, said protein forming with said species an assembly capable of emitting a signal after exposure to an excitatory wavelength, and the implementation of steps a) and b) leading to the production of a complex by interaction of said first and second partner proteins, c) subjecting said complex to said excitatory wavelength in order to obtain a first signal S1 characteristic of said complex, d) determining quantitatively or qualitatively said signal S1, e) placing the complex in contact with a medium assumed to contain a compound to be screened under conditions suitable for interaction between said compound and said complex, f) subjecting the medium obtained in step e) to said excitatory wavelength in order to obtain a second signal S2, g) determining quantitatively or qualitatively said signal S2, and h) comparing the first and second signals S1 and S2 in order to draw a conclusion relating to a possible modulation of the interaction between the first and second proteins by the screened compound.

According to one embodiment, a species that is suitable for use in the invention may be chosen from a support suitable for surface plasmon resonance, a fluorescent marker, an antibody or a combination of primary and secondary antibodies, said antibody or said secondary antibody bearing a fluorescent marker.

A protein of the invention may be combined with a species via any method known to those skilled in the art, and adapted to the nature of the support with which the protein is to be combined. A coupling method will naturally be chosen such that it does not affect the properties of interaction of the proteins of the invention with each other.

According to one embodiment, a combination between a species and a protein of the invention may be performed by chemical coupling, by molecular biology or by specific high-affinity interaction(s).

In particular, a combination may be performed via a chemical coupling, especially by means of reactive chemical functions, or via a molecular biology process.

During the use of a combination via a chemical process, the chemical functions to be reacted may be naturally present on the protein and the combined species, or may be introduced onto the protein and species prior to the chemical reaction.

As examples of reactive chemical functions that are suitable for use in the invention, mention may be, for example, made of those conventionally used in "click chemistry" reactions.

As examples of molecular biology processes that are suitable for the combination between a species and a protein of the invention, mention may be made of those conventionally performed in cloning processes especially comprising the preparation of suitable nucleic acid sequences, their ligation and their introduction into a suitable expression vector, for example a plasmid, and the transfection of the plasmid into a host cell that can enable the expression and the production of the chimeric recombinant proteins.

According to another embodiment, a species and a protein that are suitable for use in the invention may be combined with each other by means of one or more specific high-affinity interactions.

A screening process according to the invention may use fluorescence energy transfer (FRET), bioluminescence energy transfer (BRET) or surface plasmon resonance (SPR) and more particularly may use fluorescence energy transfer.

According to one embodiment, a species that is suitable for use in particular in the invention may be an antibody or a combination of primary and secondary antibodies.

An antibody that is suitable for use in the invention may be obtained via any process known to those skilled in the art, especially as described in *Antibodies: A Laboratory Manual*, Cold Spring Harbor Laboratory Press, Cold Spring Harbor, N.Y. (1990).

As antibodies that are suitable for use in the invention, mention may be made of monoclonal or polyclonal or recombinant antibodies, and also immunoglobulin fragments capable of binding an antigen and which can be produced by any genetic engineering technique known to those skilled in the art or by enzymatic or chemical cleavage of intact antibodies.

More particularly, an antibody that is suitable for use in the invention may be chosen from a monoclonal antibody, a polyclonal antibody, a "diabody", an scFv antibody, an $F(ab')^2$ antibody, an Fab' antibody, a chimeric antibody, a humanized antibody and a recombinant antibody.

According to one embodiment, an antibody that is suitable for use in the invention may have affinity for a part of the protein against which it is directed or for a specific affinity marker borne by the protein. In particular, an antibody that is suitable for use may be an antibody as described in the examples detailed below.

According to one embodiment of the present invention, one or the protein(s) of the invention may bear an affinity marker recognized by an antibody.

An affinity marker that is suitable for use in the invention may be chosen especially from the affinity markers indicated previously.

According to another embodiment, the first and the second protein are combined, respectively, with a first and a second species, said species comprising, respectively, a fluorescent group A and a fluorescent group B, said groups A and B defining an acceptor-donor pair whose fluorescence energy is suitable for performing an energy transfer by fluorescence resonance.

As examples of acceptor-donor pairs that may be used according to the present invention, mention may be made, in a nonlimiting manner, of the pairs BFP (Blue Fluorescent Protein)/GFP (Green Fluorescent Protein), CFP (Cyan Fluorescent Protein)/YFP (Yellow Fluorescent Protein), CFP/DsRed (Red Fluorescent Protein), GFP/DsRed and EuK (Europium Cryptate)/XL665. Preferably, an acceptor-donor pair that is suitable for use in the invention may be EuK/XL665.

According to one embodiment variant, the first and second species may be fluorescent markers. Such fluorescent markers may be chosen from fluorescent molecules or fluorescent proteins usually used in the field. Preferably, the fluorescent markers used may be chosen from fluorescent proteins fused by molecular biology, especially as indicated previously, to a protein of the invention.

According to another embodiment variant, the first and second species may be antibodies bearing fluorescent markers and may be suitable for binding, respectively, to a first and a second affinity marker borne, respectively, by said first and second proteins.

According to one embodiment, the signal S1 determined quantitatively or qualitatively in step d) of the process according to the invention may be a fluorescent signal obtained by irradiation at an excitatory wavelength of the fluorescence energy donor.

The signal S2, determined quantitatively or qualitatively in step f) of the process, may be a fluorescent signal obtained by irradiation at an excitatory wavelength of the fluorescence energy donor.

The fluorescence signals S1 and S2 may be measured using any device suitable for use in the invention and known to those skilled in the art. As examples of devices that are suitable for use in the invention, mention may be made of microplate readers, fluorescence microscopes, spectrofluorimeters or fluorescence scanners.

According to a preferred embodiment, a process of the invention may be performed at high throughput, in microplates, and the measurement of the fluorescence signals may be performed using a microplate reader, for example a PHERAstar (BMG) reader.

A signal S2 significantly more intense than the signal S1, in the presence of a compound to be screened, may be indicative of a compound that promotes or that is an agonist of the SASPase-FLG2 interaction.

On the other hand, a signal S2 that is significantly weaker than the signal S1, in the presence of a compound to be screened, may be indicative of a compound that destabilizes or antagonizes the SASPase-FLG2 interaction.

A compound screened by a process or a use according to the invention may be an agonist or an antagonist of the interaction between the first and second proteins.

According to a preferred embodiment of the invention, a screened compound may be capable of treating and/or preventing an esthetic disorder or a pathological disorder of the skin and/or its integuments associated with an epidermal cell differentiation and/or proliferation defect.

According to one embodiment, a screening process of the invention may also comprise at least one step that consists in evaluating the property of a screened compound to modulate the differentiation and/or proliferation of epidermal cells.

Such an evaluation may be performed in vitro or ex vivo, especially on epidermal cells in culture. The cells may be cells in lines, i.e. transformed by a virus or of tumoral origin to immortalize them. Alternatively, the cells may be primary cultures cells, i.e. derived from a tissue taken from a live organism, for example a human epidermis. Preferably, the culture cells may be keratinocytes, or even associated with fibroblasts, especially stratified. The cell cultures may be prepared according to any method known to those skilled in the art.

Also, an in vitro evaluation may be performed on a model of reconstructed epidermis. Such epidermal models may be commercially available, for example the Episkin® model.

The in vitro or ex vivo evaluation of a screened compound according to the invention may be performed via any protocol known to those skilled in the art which is directed toward comparing the given effect of a test compound with a control or standard value.

The effect of a screened compound according to the invention, in vitro or ex vivo, may be determined by measuring biological markers known as being specifically associated with the differentiation and/or proliferation of epidermal cells.

Such markers may be chosen, for example, from the measurement of the thickness of the stratum corneum, of its barrier function, or measurement of the expression and/or activation of transglutaminase I, filaggrin, caspase 14, SAS-Pase, corneodesmosin, desmoglein 1 or the protein Ki67.

These markers may be determined, for example, by qPCR, western blotting or immunofluorescence according to any protocol known to those skilled in the art.

Indications

A compound of the invention may advantageously be used for treating and/or preventing in the skin and/or its integuments an imbalance in epidermal cell differentiation and/or proliferation.

The invention is directed toward all bodily skin, including the scalp and mucous membranes, and, preferably, the skin of the face, neckline, neck, arms and forearms, and the lips, or even more preferably the skin of the face, neckline and neck and the lips.

According to another embodiment, the present invention relates to head hair, bodily hair, the eyelashes and the nails. Preferably, the invention is more particularly directed toward head hair, the eyelashes and bodily hair.

According to one embodiment, an esthetic defect under consideration in the invention may be chosen from signs of aging of the skin, a disorder of the epidermal barrier function, signs of skin dryness, a skin desquamation disorder, and a cicatrization and/or re-epithelialization defect.

According to another embodiment, an esthetic defect under consideration in the invention may be chosen from hypersudation and/or a body odor problem.

According to another embodiment, a compound of the invention may be used in cosmetics as an active agent for promoting re-epithelialization after a cutaneous scrubbing or exfoliant treatment.

A modulatory compound of the invention thus advantageously makes it possible more quickly to restore the barrier properties of the epidermis after a cosmetic treatment that may be aggressive, and to improve its protection.

According to another embodiment, a compound of the invention may be used in cosmetics as an active agent for preventing and/or treating hair loss and/or promoting hair regrowth.

According to another embodiment, a compound of the invention may be used in cosmetics as an active agent for preventing bodily hair regrowth.

According to another embodiment, a pathological disorder may be chosen from cancer, psoriasis, vitiligo, rosacea and atopic dermatitis.

The signs of aging of the skin that are more particularly under consideration in the invention may be any modification of the external appearance of the skin caused by aging, whether it is chronological and/or photoinduced, for instance wrinkles and fine lines, wizened skin, slackened skin, lack of skin elasticity and/or tonicity, thinning of the dermis and/or degradation of the collagen fibers, which results in the appearance of flaccid and wrinkled skin. Any internal modification of the skin that is not automatically reflected by a modified external appearance is also under consideration, for instance any internal degradation of the skin, particularly of the elastin fibers, or elastic fibers, following exposure to ultraviolet rays.

In particular, the signs of aging of the skin that are targeted by the invention concern thinning of an epidermis and/or a lack of firmness, elasticity, density and/or tonicity of an epidermis and/or the formation of wrinkles and fine lines.

An epidermal barrier function disorder under consideration in the invention may in particular result from external attacks of the type caused by irritant agents, for instance detergents, acids, bases, oxidizing agents, reducing agents, concentrated solvents, toxic gases or fumes, mechanical stresses, for instance friction, impacts, abrasions, in particular following an exfoliation process, peeling of the surface of the epidermis, projection of dusts or particles, shaving or epilation, thermal or climatic imbalances, for instance cold, dryness, radiations, xenobiotics, especially undesirable microorganisms, allergens, or internal attack of the type such as psychological stress.

A modulatory compound of the invention thus makes it possible to improve the barrier properties and the protection of an epidermis.

An epidermal barrier function disorder may especially be reflected by skin discomfort, sensory phenomena and especially unpleasant phenomena, especially stinging, tautness, heating and itching.

In one pathological form, a barrier function disorder may be manifested in the form of atopic dermatitis.

The signs of skin dryness that are more particularly under consideration in the invention may be any modification in the outer appearance of an epidermis, especially of a skin, due to its dehydration. A dry skin has a rough feel, and is scaly or covered with squamae, and is essentially manifested by a sensation of tautness and/or tension, linked with decreased suppleness and elasticity.

A dry skin may be pathological or non-pathological. A pathological dry skin may be represented by atopic dermatitis and ichthyosis.

A non-pathological dry skin may be represented by senile skin, characterized especially by a general decrease in skin metabolism with age, fragile skin, which may be characterized by skin that is very sensitive to external factors and often accompanied by erythema and rosacea, and common xerosis, of probable genetic origin and manifesting mainly on the face, the limbs and the back of the hands.

A desquamation disorder that is more particularly under consideration in the invention may be a desquamation disorder of the skin or the scalp.

A scalp desquamation disorder may appear in the form of dandruff, especially dry dandruff.

Dry dandruff is formed from small squamae which readily detach from the epidermis and which, on clinical examination, do not appear inflammatory.

The cicatrization and re-epithelialization defects that are under consideration in the invention may especially be manifested in the form of epidermal impairment or scarring defects of the epidermis resulting from surgical interventions or following an esthetic or pathological disorder of the epidermis, such as acne scars or signs of stretchmarks. The re-epithelialization defects that are under consideration in the invention may also occur following chemical or mechanical exfoliation of the skin or in the case of elderly skin. A modulatory compound may be used before or after exfoliation to promote re-establishment of the barrier functions of the epidermis.

The body odor under consideration in the invention may especially be any undesirable odor that may be perceived as being offensive, or even incapacitating, by the person producing it and/or the people in his vicinity.

It is more particularly a case of odor noted on areas of the body that undergo heavy sweating and more particularly the axillary areas, especially the armpits, or the feet, the mammary areolae and the perianal region, where the majority of the sweat glands, in particular the apocrine glands, are found.

Body odor is especially that arising from sudation, or even hypersudation, and/or from the bacterial degradation of sweat and more particularly of apocrine sweat.

Compositions

A compound of the invention is advantageously formulated in a composition that may be in any galenical form normally available for the intended indication and mode of administration.

A composition according to the invention comprises a physiologically or pharmaceutically acceptable medium.

A composition according to the invention may be administered orally, parenterally or topically.

Preferably, a composition of the invention may be administered topically.

According to one embodiment, a topical composition according to the invention may advantageously be formulated in any galenical form that is suitable for caring for the skin and mucous membranes and may be in the form of ointments, creams, milks, pomades, powders, impregnated pads, solutions, gels, sprays, lotions or suspensions. It may also be in the form of lipid or polymeric microspheres, nanospheres or vesicles or polymer patches and hydrogels allowing controlled release. These topical compositions may be either in anhydrous form or in aqueous form according to the dermocosmetic indication.

A composition intended for topical administration may be an aqueous, aqueous-alcoholic or oily solution, a solution or dispersion of the lotion or serum type, an emulsion of liquid or semiliquid consistency of the milk type, obtained by dispersing a fatty phase in an aqueous phase (O/W) or conversely (W/O), a suspension or an emulsion, of soft, semisolid or solid consistency, of the cream type or of the aqueous or anhydrous gel type, a multiple emulsion (W/O/W or O/W/O), a microemulsion, a nanoemulsion, a preparation of microcapsules, a preparation of microparticles, a vesicular dispersion of ionic and/or nonionic type, or a wax/aqueous phase dispersion.

According to a preferred embodiment, a topical composition may be in the form of a solution, a cream, a gel, an emulsion, a foam or an aerosol composition containing a propellant.

According to a preferred embodiment, a topical composition may also be in the form of a transdermal system allowing active or passive release of the active agent(s) transdermally, for example of the patch or patch gel (hydrogel) type.

These compositions are prepared according to the usual methods.

A composition according to the invention may constitute a composition for treating or caring for the skin or the scalp, or an antisun or artificial tanning composition, or alternatively a skin cleansing or makeup-removing product, a deodorant product or a fragrancing compound, a cleansing, protective, medicated or care cream, a skincare lotion, gel or foam, a cleansing or disinfectant lotion, a bath composition or a deodorant composition. It may also be in the form of a coloring or non-coloring, medicated or non-medicated shampoo, or a hair conditioner. A composition according to the invention may also consist of a solid preparation constituting a soap or a cleansing bar.

Such a composition may then be uncolored or weakly colored, and may optionally contain additional cosmetic or dermatological active agents, especially as indicated below. It may then be used as a care base for the skin or the lips, for example in the form of a lip balm, for protecting the lips against the cold and/or sunlight and/or the wind, such as a day or night care cream for facial and/or bodily skin.

A composition according to the invention may also constitute a colored cosmetic composition and especially a makeup composition for the skin and/or mucous membranes, and in particular such a composition may be a foundation, a blusher, a face powder, an eyeshadow, a concealer compound in stick form, a lipstick or a lip gloss, optionally having care or treating properties. Preferably, it may be a colored (beige or green) makeup composition for correcting the color of the complexion.

A composition according to the invention may also constitute a composition for making up or caring for the nails or the eyelashes.

When a composition of the invention is an emulsion, the proportion of the fatty phase may range from 5% to 80% by weight and preferably from 10% to 50% by weight relative to the total weight of the composition. The oils, emulsifiers and coemulsifiers used in the composition in emulsion form are chosen from those conventionally used in cosmetics and/or dermatology. The emulsifier and the coemulsifier may be present in the composition in a proportion ranging from 0.3% to 30% by weight and preferably from 0.5% to 20% by weight relative to the total weight of the composition.

When the composition of the invention is an oily solution or gel, the fatty phase may represent more than 90% of the total weight of the composition.

In the case of a composition in accordance with the invention for oral administration, the use of an ingestible support is preferred.

The ingestible support may be of diverse nature according to the type of composition under consideration.

Tablets, gel capsules or lozenges, suspensions, oral supplements in dry form and oral supplements in liquid form are thus especially suitable for use as food supports.

Milk, yoghurt, cheese, fermented milks, milk-based fermented products, ice creams, cereal-based products or fermented cereal-based products, milk-based powders, infant and baby formulae, food products of confectionery, chocolate or cereal type, and animal feed in particular for pets, are also suitable as food supports.

The term "oral composition" means, for example, nutritional, nutraceutical, cosmeceutical or pharmaceutical compositions comprising at least one compound according to the invention.

The formulation of the oral compositions according to the invention may be performed via any common process known to those skilled in the art for producing drinkable solutions, coated tablets, gel capsules, gels, emulsions, tablets to be swallowed or chewed, capsules, especially soft or hard capsules, granules to be dissolved, syrups, solid or liquid foods and hydrogels allowing controlled release, food bars, powders, in compacted or non-compacted form, liquid solutions or suspensions, confectioneries, fermented milks, fermented cheeses, chewing gums, toothpastes or spray solutions.

The oral compositions may be either in anhydrous form or in aqueous form according to the dermocosmetic indication.

A compound of the invention may moreover be formulated with the usual excipients and components for such oral compositions or food supplements, i.e. especially fatty and/or aqueous components, humectants, thickeners, preserving agents, texture agents, taste agents and/or coating agents, and/or antioxidants.

The formulating agents and excipients for oral compositions, and especially for food supplements, are known in this field and will not be the subject of a detailed description herein.

In particular, a composition according to the invention may be a food composition for human consumption. This may be, in particular, nutritional whole foods, drinks, mineral waters, soups, dietary supplements and replacement foods, nutritional bars, confectioneries, fermented or nonfermented milk-based products, yoghurts, milk-based powders, enteral nutritional products, infant and/or baby compositions, fermented or nonfermented cereal-based products, ice creams, chocolate, coffee, "culinary" products such as mayonnaise, tomato puree or salad dressings.

The composition according to the invention may also be intended for animals, especially pets, such as cats and dogs, and may be formulated in the form of animal feed or animal feed supplements.

According to another embodiment, a compound that is suitable for use in the invention may be used parenterally, in particular subcutaneously or intradermally.

In such a use, an active agent that is suitable for use in the invention may be conditioned in the form of an aqueous or nonaqueous sterile isotonic solution, in the form of a dispersion, suspension or emulsion prepared, where appropriate, just before administration, using a sterile powder, for example a freeze-dried powder, which is then reconstituted in the form of an injectable sterile solution or a dispersion at the time of use thereof.

The term "sterile" is intended to qualify a formulation that is capable of ensuring the harmlessness required for intraepidermal and/or intradermal and/or subcutaneous administration.

A composition that is suitable for use in the invention may comprise any excipient usually used in the field of injectable sterile solutions.

The parenteral administration of a composition of the invention may be performed via any injection technique and/or device that is suitable for intraepidermal and/or intradermal and/or subcutaneous injection. Thus, such an administration may also be performed by mesotherapy.

Via the parenteral route, administration using a systemic patch may be preferred.

A composition according to the invention may also comprise at least one cosmetically or dermatologically acceptable ingredient. The amounts of these various ingredients are those conventionally used in the field under consideration, and are especially determined so as not to affect the desired properties for a compound of the invention or for a composition of the invention.

A cosmetic or dermatological active agent that is suitable for use in the invention may be chosen from moisturizers, vitamins, essential fatty acids, sphingolipids, UV-screening agents, antioxidants, antiacne agents, antiinflammatory agents, tanning agents (in the absence of UV radiation), depigmenting agents, matting agents, proteins or protein hydrolyzates, amino acids, polyols, urea, allantoin, sugars and sugar derivatives, water-soluble vitamins, plant extracts and hydroxy acids, retinol and derivatives thereof, tocopherol and derivatives thereof, essential fatty acids, ceramides, essential oils, salicylic acid and derivatives thereof, vitamin D3 and derivatives thereof, retinoids and derivatives thereof, PPAR-gamma agonists, hair-loss counteractants or hair regrowth agents such as potassium channel openers, and antiandrogens, and mixtures thereof.

A composition of the invention may comprise any formulating agent usually used in the field.

As hydrophilic gelling agents that are suitable for use in the invention, mention may be made of carboxylic polymers such as carbomer, acrylic copolymers such as acrylate/alkyl acrylate copolymers, polyacrylamides and especially the mixture of polyacrylamide, $C_{13-14}$ isoparaffin and Laureth-7 sold under the name Sepigel 305® by the company SEPPIC, polysaccharides, for instance cellulose derivatives such as hydroxyalkylcelluloses and in particular hydroxypropylcelluloses and hydroxyethylcelluloses, natural gums such as guar gum, locust bean gum and xanthan gum, and clays.

As lipophilic gelling agents that are suitable for use in the invention, mention may be made of modified clays, for instance bentones, metal salts of fatty acids, for instance aluminum stearates and hydrophobic silica, or else ethylcellulose and polyethylene.

As surfactants that may be used in the invention, mention may be made, for example, of glyceryl stearate, polysorbate 60, the mixture of cetylstearyl alcohol/cetylstearyl alcohol oxyethylenated with 33 mol of ethylene oxide sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyl dimethicone copolyol, and sorbitan monostearate or tristearate, PEG-40 stearate and oxyethylenated (20 OE) sorbitan monostearate.

As fillers that are suitable for use in the invention, mention may be made of talc, mica, silica, kaolin, precipitated calcium carbonate, magnesium carbonate, magnesium hydrogen carbonate, hydroxyapatite, boron nitride, polyamide powders (Nylon® Orgasol from Atochem), poly-β-alanine powder and polyethylene powder, polytetrafluoroethylene powders (Teflon®), lauroyllysine, starch, tetrafluoroethylene polymer powders, hollow polymer microspheres such as Expancel (Nobel Industrie), metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone. It may in particular be a hexamethylene diisocyanate/trimethylol hexyllactone polymer. Such particles are especially commercially available, for example, under the name Plastic Powder D-400® or Plastic Powder D-800® from the company Toshiki, and mixtures thereof.

As odor absorbers that are suitable for use in the invention, mention may be made of zeolites and cyclodextrins.

A dyestuff that is suitable for use in the invention is a compound that is capable of producing a colored optical effect when it is formulated in sufficient amount in a suitable cosmetic medium. As dyestuffs that may be used, mention may be made of pigments, nacres, glitter flakes, liposoluble dyes and water-soluble dyes, and mixtures thereof.

The pigments may be chosen from mineral pigments, organic pigments and composite pigments (i.e. pigments based on mineral and/or organic materials). The pigments may be chosen from monochromatic pigments, lakes, nacres, and pigments with an optical effect, for instance reflective pigments and goniochromatic pigments.

A film-forming polymer that is suitable for use in the invention may be chosen from radical polymers, polycondensates and polymers of natural origin, and mixtures thereof. The term "polymers" means compounds comprising at least two repeating units, preferably at least three repeating units and more especially at least 10 repeating units.

The radical polymers may be chosen, for example, from acrylic polymers and/or vinyl polymers. According to the invention, the polycondensates may be chosen from polyurethanes, polyesters, polyester amides, polyamides, fatty-chain polyesters and epoxy ester resins, and mixtures thereof. Polymers of natural origin that may be mentioned include shellac and sandarac gum.

The term "semicrystalline polymer" means polymers comprising a crystallizable portion, a crystallizable pendent chain or a crystallizable block in the backbone, and an amorphous portion in the backbone, and having a first-order reversible phase-change temperature, in particular of melting (solid-liquid transition). A semicrystalline polymer may be chosen from block copolymers comprising at least one crystallizable block and at least one amorphous block, homopolymers and copolymers bearing at least one crystallizable side chain per repeating unit, and mixtures thereof. Such polymers are described, for example, in EP 1 396 259. As a particular example of a structuring semicrystalline polymer that may be used according to the invention, mention may be made of the Intelimer® products from the company Landec described in the brochure Intelimer® polymers, Landec IP22 (Rev. 4-97). These polymers are in solid form at room temperature (25° C.). They bear crystallizable side chains.

As fatty substances that may be used in the invention, mention may be made of volatile oils and nonvolatile oils, for instance mineral oils such as hydrogenated polyisobutene and liquid petroleum jelly, plant oils, for instance a liquid fraction of shea butter, sunflower oil and apricot kernel oil, animal oils, for instance perhydrosqualene, synthetic oils, in particular purcellin oil, isopropyl myristate and ethylhexyl palmitate, unsaturated fatty acids, silicone oils and fluoro oils, for instance perfluoropolyethers.

A pasty or solid fatty substance that may be present in a composition of the invention may be, for example, a fatty acid chosen from fatty acids comprising from 8 to 30 carbon atoms, such as stearic acid, lauric acid, palmitic acid and oleic acid; a wax chosen from waxes such as lanolin, beeswax, carnauba wax or candelilla wax, paraffin wax, lignite wax or microcrystalline waxes, ceresin or ozokerite, synthetic waxes such as polyethylene waxes and Fischer-Tropsch waxes; a gum chosen from silicone gums (dimethiconol), a pasty compound, for instance polymeric or nonpolymeric silicones, esters of an oligomeric glycerol, arachidyl propionate and fatty acid triglycerides, and derivatives thereof, and mixtures thereof.

As solvents that may be used in the invention, mention may be made of lower alcohols, for instance ethanol, isopropanol and propylene glycol.

The composition of the invention may also advantageously contain a spring and/or mineral water, chosen in particular from Vittel water, waters from the Vichy Basin, and la Roche Posay water.

Conditioning Article

A conditioning article of the invention will naturally be chosen by a person skilled in the art according to the galenical form of the composition to be conditioned.

Thus, for liquid compositions, use may be made of containers consisting of a rigid envelope comprising means for dispensing the composition. These dispensing means may be a simple orifice, which is blocked by a removable cap, or a push button associated with a pump for expelling a part of the composition contained in the container. The compositions of the invention in liquid form may also be conditioned in containers of aerosol can type.

A composition of the invention in semiliquid or pasty form may be advantageously conditioned in a jar, a tube of cream, or in a container with supple or deformable walls and having an orifice that can be stoppered with a removable lid, the composition being expelled through the orifice by pressing on the walls, or a bottle equipped with a push button and a pump as indicated previously.

According to a particular embodiment, a conditioning article that is suitable for receiving a composition according to the invention may be made of glass, metal, alloy, coated papers such as wax-coated papers, for instance papers coated with beeswax, which especially have properties as a natural preserving agent.

Alternatively, a composition according to the invention may be stored under vacuum, in a hermetically sealed airtight compartment, like, for example, a brick-carton under vacuum, commonly used in the food sector.

The conditioning article may be at least partly made of plastics or other suitable polymeric materials.

According to a particular embodiment, a composition according to the invention may be conditioned "under a protective atmosphere". Conditioning "under a protective atmosphere" consists in modifying the composition of the internal atmosphere of a packaging with the aim of improving the shelf-life of its content. This technique consists in reducing the level of oxygen in order to slow down the growth of aerobic life forms and oxidation reactions. The oxygen removed can be replaced with other gases.

According to a particular embodiment, the conditioning article can also be made using materials which make it possible to isolate the composition from any light sources.

The conditioning article can also be at least partly made of thermal insulation materials. By way of examples of materials of this type, mention may be made of fabrics, fabrics made of glass fibers coated with silicone, textiles based on ceramic fibers, cellulose fibers, polystyrene, styrofoam, and packaging films. A cold gel or liquid may also be used as thermal insulation material.

According to a particular embodiment, the conditioning article may be disposable and opened just before its use by the consumer.

According to one embodiment, a composition of the invention formulated in solid form may be conditioned, for example, in a jar or a tube for a stick, for example a lipstick tube.

Cosmetic Treatment Process

As indicated previously, the invention relates to a cosmetic process dedicated to individuals with esthetic defects of the skin and/or its integuments associated with an epidermal cell differentiation and/or proliferation defect.

An individual concerned by a cosmetic treatment process of the invention is naturally an individual who has, or who is liable to have, at least one of the cosmetic care indications defined previously.

A process of the invention makes it possible to treat an esthetic defect of the skin and/or its integuments as defined previously.

A process according to the invention may also comprise a step that consists in observing a reduction or even disappearance of the esthetic defect of the skin and/or its integuments, or alternatively an improvement in the esthetic appearance of the skin and/or its integuments.

Preferably, a process according to the invention may be performed topically, orally or parenterally.

Even more preferentially, a process according to the invention is performed topically or orally.

A process according to the invention may be performed, topically, especially by applying to the skin and/or its integuments at least one coat of a cosmetic or dermatological composition comprising, as active agent, at least one compound of the invention, and more particularly a cosmetic composition as defined previously.

According to one embodiment, a process of the invention may comprise a step of applying at least one coat of a cosmetic or dermatological composition comprising, as active agent, at least one compound of the invention, to the skin of the body, especially the skin of the face or the neckline, or to the scalp, the lips, the hair, the eyelashes or the nails.

Preferably, a process of the invention may comprise the topical application to the skin or the lips, especially the skin of the face and the neckline, of at least one coat of a composition of the invention.

Advantageously, a topical process of the invention may comprise the application of a composition in accordance with the invention, for example in the form of a mask, especially to facial skin.

Such an administration may be performed according to the usual techniques for using these compositions. For example, it may consist of the application of creams, gels, sera or lotions to the skin or mucous membranes.

A topical cosmetic process according to the invention can be carried out on a daily basis for example, at a rate of, for example, a single administration per day or one administration twice a day, for example once in the morning and once in the evening.

A topical cosmetic process according to the invention can be carried out over a time period ranging from one week to several weeks, or even several months, this period moreover possibly being repeated after periods without treatment, for several months or even several years.

By way of example, the topical administration of a compound according to the invention may be repeated, for example, 2 to 3 times a day or more and generally over an extended period of at least 4 weeks, or even 4 to 15 weeks, with, where appropriate, one or more periods of interruption.

A process of the invention may advantageously comprise the application of a composition of the invention, in combination, simultaneously, successively or separately over time, with the administration of an additional cosmetic or dermatological composition distinct from the composition of the invention and intended for caring for or making up the skin and/or its integuments.

Any additional cosmetic or dermatological composition may be suitable for use in the invention, with the proviso, naturally, that its combination with a composition of the invention does not affect the properties desired for the same. A person skilled in the art knows how to access, on the basis of his knowledge, the additional cosmetic or dermatological compositions that may be suitable for use.

According to one embodiment, this additional composition may be administered topically to the skin and/or its integuments.

According to another embodiment, a process of the invention may comprise the application to the skin and/or its integuments of a composition of the invention in combination with a successive topical application to said skin and/or said integuments of an additional cosmetic or dermatological composition.

The composition of the invention and the additional composition may be applied one on top of the other in a "two-stroke application" cosmetic act.

According to one embodiment, a process according to the invention may comprise the application to the skin and/or its integuments, as a first coat or "base coat", of a composition of the invention, and, as a second coat or "top coat", of a coat of an additional composition as defined previously.

According to an embodiment variant, the first coat may comprise the additional composition, and the second coat may comprise a composition of the invention.

A cosmetic process of the invention may be performed orally, especially by administration of at least one cosmetically directed food composition comprising as active agent at least one compound of the invention, and in particular a cosmetically directed food composition as defined above.

A composition according to the invention may be administered in a single dose per day or in fractional doses over the day, for example two to three times a day.

An oral cosmetic process may be performed over a time period ranging from one week to several weeks, or even several months, this period moreover possibly being repeated after periods without treatment, for several months or even several years.

By way of example, the oral administration as active agent of a compound according to the invention may be performed at a rate, for example, of three times a day, more generally over a prolonged period of at least 4 weeks, or even 4 to 15 weeks, optionally comprising one or more periods of stoppage or being repeated after a period of stoppage.

A cosmetic process according to the invention may also be performed parenterally. The parenteral implementation of a cosmetic process of the invention is carried out with the exclusion of any surgical intervention and is merely aimed at performing a surface treatment of the skin for esthetic purposes.

A parenteral administration may be performed, for example, by any injection technique or device that is suitable for intraepidermal and/or intradermal and/or subcutaneous injection. Such an administration may be performed by mesotherapy.

It is alternatively possible, parenterally, to favor administration using a systemic patch.

By way of example, the parenteral administration of a compound of the invention may be performed, for example, at least once a month, or even at least once a week, and more generally at least once a day, over a more or less prolonged period which may be, for example, at least four weeks, or even 4 to 15 weeks, optionally comprising one or more periods of stoppage, or being repeated after a period of stoppage.

According to another aspect, the present invention relates to the use of an effective amount of at least one compound of the invention for the preparation and/or improvement of a multilayer cellular model, especially of epidermal or mucous type, and in particular a model of reconstructed skin.

Advantageously, a compound of the invention is added to the culture medium in which the multilayer cellular model is cultured. The moment and duration of incubation of the cellular model in the presence of a compound of the invention are naturally adapted by a person skilled in the art as a function of the cellular model to be obtained and of the compound used.

For the purposes of the invention, the term "model of reconstructed skin" is intended to denote a model in which are combined various cell types, especially such as the natural constituents of the skin, for instance keratinocytes, fibroblasts, Langerhans cells and melanocytes. The cells of fibroblast type can optionally be irradiated.

Such models and the preparation thereof are known to those skilled in the art.

In the description and the examples that follow, unless otherwise mentioned, the percentages are weight percentages and the ranges of values written in the form "between . . . and . . . " include the stated lower and upper limits.

For the purposes of the present invention, "one" should be understood, unless otherwise indicated, in the sense of "at least one".

The examples given below are presented as non-limiting illustrations of the invention.

FIGURES

FIG. 1: illustrates the evolution of the enzymatic hydrolysis of the fluorescent substrate Dabcyl-QIDRIMEK-Edans by a recombinant SASPase (28 kDa) in the presence of increasing concentrations of active recombinant FLG2 (Hs complex=thioredoxin-His-S.Tag-FLG2$_{2-213}$; black histogram) or inactive recombinant FLG2 (AbD complex=thioredoxin-His-S.Tag-FLG2$_{81-212}$; gray histogram) expressed in multiples (0; 0.01; 0.02; 0.04; 0.06; 0.16; 0.3; 0.63; 1.25; 2.50; 5.00 and 10.00) of the initial SASPase concentration (0.025 mg/ml). The enzymatic reaction is performed in an acetate/acetic acid buffer. The FIGURE illustrates the mean±sem of an experiment performed in duplicate.

EXAMPLES

Example 1

Enzymatic Activation of SASPase by FLG2
a—Materials and Methods
Two forms of recombinant filaggrin-2 (FLG2) corresponding, respectively, to the amino acid sequences 2-213, active form, and 81-212, inactive form, of Q5D862 (Uniprot/Swissprot ref.) fused, at their N-terminal end, to a thioredoxin-His-S.Tag (THX-His-S-tag) affinity marker were prepared in a parental plasmid pET32c (Novagen) or pEB6 (HBGX) (FLG2$_{2-213}$-S-His-THX and FLG2$_{81-212}$-S-His-THX).

These recombinant chimeric proteins are identified hereinbelow under the names FLG2-Hs=FLG2$_{2-213}$-S-His-THX (active form) and FLG2-AbD=FLG2$_{81-212}$-S-His-THX (inactive form).

A 28-kDa recombinant SASPase corresponding to the amino acid sequence 85 to 343 of the sequence Q53RT3 (Uniprot/Swissprot ref.) was prepared as described by Bernard et al. (J. Invest. Dermatol., 2005, 125: 278-287) (SASPase$_{85-343}$).

The SASPase was dissolved in a PBS buffer and used at a final concentration of 0.025 mg/ml in the presence of a final concentration of a colorimetric substrate Dabcyl-QID-RIMEK-Edans of 0.01 mM (Production Jerini Peptide Ref. D17: JPT Peptide Technologies GmbH).

FLG2-Hs and FLG2-AbD are used at concentrations corresponding to 0.01, 0.02, 0.04, 0.08, 0.16, 0.31, 0.63, 1.25, 2.5, 5 or 10 times the final concentration of SASPase, i.e. 0.025 mg/ml.

SASPase and FLG2-Hs, or FLG2-AbD, are incubated at 37° C. in a 0.1 M acetate/acetic acid buffer at pH 5.5 containing 150 mM of NaCl, in the presence of Dabcyl-QIDRIMEK-Edans.

The hydrolysis of the colorimetric substrate by the activated SASPase leads to the separation of the Edans fluorochrome and of its Dabcyl deactivator (or quencher), and to an increase in the fluorescence of Edans.

Measurement of the fluorescent signal is performed at $\lambda_{ex}$ 340 nm/$\lambda_{ex}$ 490 nm. The fluorescence is read every 10 minutes for 1 hour 30 minutes at 37° C., with a Spectramax M5e (Molecular Devices).

b—Results
The results obtained show that the enzymatic activity of the SASPase is significantly increased in the presence of an increasing concentration of active FLG2-Hs, whereas it remains virtually unchanged in the presence of inactive FLG2-AbD (see FIG. 1).

These results show that FLG2 interacts with SASPase, and stimulates its proteolytic activity. Such an activation is obtained at and above an FLG2 concentration equivalent to that of the SASPase.

Example 2

Screening of Agents that Modulate the SASPase-FLG2 Interaction

The SASPase-FLG2 interaction, and the stimulation of the proteolytic activity of SASPase resulting therefrom, were exploited in a process for screening active compounds that are capable of modulating this interaction.

The process developed is based on the FLG2-SASPase interaction and uses the homogeneous time-resolved fluorescence (or HTRF) technique.

A recombinant SASPase protein (comprising the amino acid sequence 85-343 of Q53RT3) mutated at its active site (D212A of Q53RT3) and fused with the GST (glutathione S-transferase from *Schistosoma japonicum*) affinity marker, at its C-terminal end, was prepared in the vector pGEX-4-T3 (GenBank U13855) (SASPase$_{85-343D212A}$-GST). The D212A mutation was introduced to inactivate the SASPase and to promote a stable interaction with FLG2.

A recombinant FLG2 protein (comprising the amino acid sequence 2-213 of Q5D862) fused to the thioredoxin-His-S.Tag affinity marker, at its N-terminal end, was prepared as follows (FLG2$_{2-213}$-S-His-Thx).

The plasmids obtained are used to transform competent *E. coli* BL21DE3 bacteria. After transformation of the plasmid corresponding to the protein in the bacteria, 4 ml of preculture were incubated overnight at 37° C. with stirring (250 rpm). The preculture was added to 100 mL of culture medium (LB+ampicillin) and the assembly is placed at 37° C. with stirring until an optical density at 600 nm of at least 0.8 is obtained.

The transformed bacteria are then induced in the presence of 1 mM IPTG overnight at 16° C. with stirring, and then centrifuged and lyzed by ultrasonication. The chimeric peptides are purified by affinity for the HIS or GST tag on a suitable resin, and then dialyzed against a pH 8, 1×PBS buffer. The chimeric proteins obtained are then assayed by the Bradford method.

Antibodies recognizing, respectively, the affinity markers GST or His-S.Tag, and bearing, respectively, an EuK fluorescence donor group (europium cryptate $\lambda_{ex}$ 337 nm/$\lambda_{em}$ 620 nm) or an XL1665 fluorescence receiver group ($\lambda_{ex}$ 570-630 nm/$\lambda_{em}$ 665 nm) are used to monitor the peptide-SASPase interaction.

Such antibodies are commercially available, for example from the company Cisbio International under the references 61GSTKLB (anti-GST K antibody) or 61HISKLB (anti-6HIS K antibody).

The SASPase-FLG2 interaction was observed by fluorescence energy transfer (FRET) between the fluorescent markers Euk and XL1665. The Euk fluorescence donor was excited at $\lambda_{ex}$ 337 nm and the fluorescence emission of the XL1665 fluorescence acceptor was measured at $\lambda_{em}$ 665 nm.

The Euk fluorescence emission at $\lambda_{em}$ 620 nm, taking place independently of the interaction between SASPase and FLG2, was used to normalize the signal. Thus, for each point, a ratio $\lambda_{em}$ 665/$\lambda_{em}$ 620 is determined.

The screening process was performed in 384-well plates using a Janus robot from Perkin-Elmer in a PBS phosphate buffer at pH 7.4.

The tests are performed in quadruplicate. The positive control (100% signal) is obtained in the presence of the recombinant proteins, DMSO and antibodies labeled with the fluorophores. The negative control (0% signal or background) is obtained in the presence of protein dilution buffer (free of proteins), DMSO and antibodies labeled with the fluorophores.

The DMSO is used at a final concentration of 2.5%.

The recombinant proteins SASPase$_{85-343D212A}$-GST and FLG2$_{2-213}$-S-His-THX were used at respective final concentrations of 50 nM and 200 nM.

The test compounds were used at final concentrations of $5\times10^{-9}$ M; $1.5\times10^{-8}$ M; $4.6\times10^{-8}$ M; $1.4\times10$ M; $4.1\times10^{-7}$ M; $1.2\times10^{-6}$ M; $1.1\times10^{-5}$ M; $3.3\times10^{-5}$ M and $1\times10^{-4}$ M.

A buffer, or dilution solution free of compound, was used as control.

The SASPase$_{85-343D212A}$-GST and the test compounds were preincubated at 4° C. for 60 minutes, and FLG2-His-THX was then added, and the assembly was incubated at 4° C. overnight.

The specific antibodies for each of the chimeric proteins were then added, at a final dilution of 1/400 in a KF (potassium fluoride) buffer (Acros ref. 20135).

The mixture was incubated overnight at 4° C. before reading the fluorescence ($\lambda_{ex}$ 337 nm/$\lambda_{em}$ 665 nm, and normalization at $k_{em}$ 620 nm) using a Pherastar reader (BMG).

The calculation of the result is performed as follows.

The mean of the ratios $\lambda_{em}$ 665/$\lambda_{em}$ 620 for the positive controls is determined: S.

The mean of the ratios $\lambda_{em}$ 665/$\lambda_{em}$ 620 for the negative controls is determined: B.

The mean of the ratios $\lambda_{em}$ 665/$\lambda_{em}$ 620 for each point of the concentration range of the test compounds is determined: C.

For each point of the concentration range of the test compounds, an activity percentage A is determined via the formula: $A=(C-B)/(S-B)$.

A dose-response curve was established with the software GraphPad Prism® V.5.02 using the equation of a sigmoidal dose-response curve with a variable gradient coefficient, according to the indications in the software.

The IC$_{50}$ (concentration inhibiting 50% of the effect) or the EC$_{50}$ (concentration activating 50% of the effect) are determined by taking the mid-height concentration, between the bottom and the plateau phase of the curve obtained.

A decrease of A is indicative of the presence of compounds that are capable of preventing or destabilizing the interaction between SASPase and FLG2.

An increase of A is indicative of the presence of compounds that are capable of stabilizing or promoting the interaction between SASPase and FLG2.

The screening of a molecule databank HBGXS10 (ChemDiv Discovery Chemistry Collection Public Database (Order Number: 4477-2039), ChemDiv, Inc. San Diego, USA) made it possible to identify the compound, referred to as "M7", of formula (II) below:

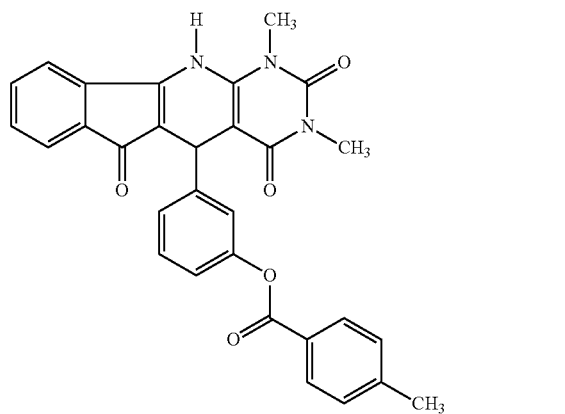

(Formula II)

This compound led to an inhibition of the SASPase-FLG2 interaction and has an IC$_{50}$ of about 2 µM.

The screening protocol of the invention thus proves to be particularly advantageous for identifying novel active compounds that are capable of positively or negatively modulating the SASPase-FLG2 interaction.

The novel compounds may advantageously be used with regard to esthetic defects or pathological disorders of the skin and its integuments resulting from an imbalance in epidermal cell proliferation and/or differentiation, and in particular aging of the skin and skin dryness.

Example 3

Effect of Compound "M7" on the Differentiation and/or Proliferation of Epidermal Cells a—Materials and Methods A model of reconstructed human epidermis Episkin J6 (reference 09-EPIS-015) was cultured by immersion in Episkin differentiation medium, 3.5 ml under insert in an oven at 37° C., 5% $CO_2$, the medium being changed every 2 days.

The compound "M7" was tested at concentrations of 10 µM, 1 µM and 0.5 µM by incubation of the epidermal model with a differentiation culture medium supplied by EpiSkin®, comprising the compound at the test concentration or a buffer solution as control (DMSO at 0.1% final).

The effect of the compound "M7" on the differentiation and/or proliferation of epidermal cells is evaluated by measuring the thickness of the stratum corneum, and measurement of the expression and/or activation of transglutaminase I (TGI), caspase 14, SASPase, corneodesmosin, desmoglein 1 or protein Ki67.

The thickness of the stratum corneum was estimated by histological observation on slices.

The activation, expression and maturation of TGI, filaggrin, caspase 14, SASPase, corneodesmosin and desmoglein 1 were determined by western blotting.

The activation, expression and maturation of Ki67 were determined by immunofluorescence on frozen slices.

For the western blotting, the soluble proteins, TGI, caspase 14, corneodesmosin and SASPase were extracted from two Episkin® nacelles with a manual potter in 1 ml of "native +" buffer (TBS, 1M NaCl, 0.1% Tween 20). The extract is centrifuged at 14 000 rpm, at 4° C. for 10 minutes. The supernatant obtained is filtered through a 0.45 µm Millipore filter (millex) and the proteins are then quantified by the BCA method (Pierce). The protein concentrations are equilibrated to 625 µg/ml final.

The extracts are deposited on a 10-20% Criterion gel (ref.: 345-0044 Bio-Rad) according to the supplier's protocol, and are then transferred onto a PVDF membrane via the semidry method.

The western blotting immunochemical detection is performed according to a standard protocol carried out with primary antibodies specific for the target and secondary antibodies coupled to HRP. Revelation is performed with the kits ECL; ECL plus; ECL advanced (Amersham) according to the necessary sensitivity and according to the supplier's protocol. The photon imaging apparatus used is the Fluor S MultiImager (Bio-Rad).

For TGI, primary antibody: Covalab pab 0061 at 1/100 produced in rabbits; secondary antibody: HRP-coupled anti-rabbit antibody at 1/4000: Bio-rad 170-6515

For caspase 14, primary antibody: Santa Cruz sc-5628 at 1/500 produced in rabbits; secondary antibody: HRP-coupled anti-rabbit antibody at 1/400: Bio-rad 170-6515

For corneodesmosin, primary antibody: Abnova 1041-M01 at 1/5000 produced in mice; secondary antibody: HRP-coupled anti-mouse antibody at 1/4000: Bio-rad 170-6516

For SASPase, primary antibody: Covalab 7H9a105 at 1/2000 produced in mice; secondary antibody: HRP-coupled anti-mouse antibody at 1/4000: Bio-rad 170-6516

For the western blotting of filaggrin and desmoglein 1, these proteins are extracted from the pellet obtained during the extraction of the "soluble" proteins. The pellets are ground with an electric potter in 200 µl of whole Laemmli buffer (0.0625 mM Tris; 2% SDS; 200 mM DTT; 10% glycerol) and then heated at 90° C. for 10 minutes and finally centrifuged for 10 minutes at 14 000 rpm at room temperature.

The supernatants obtained are assayed for proteins via the Bradford method (cytoskeleton). The total protein concentrations are equilibrated to 1 mg/ml final. A western blotting protocol identical to the previous one is applied.

For filaggrin, primary antibody: Abcam ab24584 at 1/1000 produced in rabbits; secondary antibody: HRP-coupled anti-rabbit antibody at 1/4000: Bio-rad 170-6515

For desmoglein 1, primary antibody: Progen 61002 at 1/100 produced in mice; secondary antibody: HRP-coupled anti-mouse antibody at 1/4000: Bio-rad 170-6516

The immunofluorescence labeling on frozen slices is performed using a standard protocol, with a PBS buffer; 0.2% BSA for the steps of washing and incubation of the primary and secondary antibodies, and with a PBS buffer; 5% BSA for the step for blocking the nonspecific sites.

For the detection of Ki67, primary antibody: Novocastra mm1 at 1/20 produced in mice; secondary antibody: AlexaFLuor A488-coupled anti-mouse antibody at 1/1000 (Molecular Probes A11017). The visualization and image capture apparatus is a Leica® optical microscope.

b—Results

The application of compound "M7" led to thickening of the stratum corneum, which was observable on histological slices by optical microscopy, at and above the lowest concentration tested.

An increase in the expression and activation of TGI, caspase 14, SASPase, corneodesmosin and desmoglein was observed in the Episkin epidermis cultured in the presence of "M7".

The expression of these proteins is combined with differentiation of the cells in the epidermis.

A decrease in the activation and expression of the protein Ki67 was also observed. This protein is associated with stoppage of the proliferation of epidermal cells.

The thickening of the stratum corneum and the increase in the expression and activation of the proteins transglutaminase I, caspase 14, SASPase, corneodesmosin and desmoglein are characteristics of late differentiation of the epidermis.

The compound "M7" thus proves to have the property of modulating the proliferation and differentiation of epidermal cells.

Such a compound thus proves to be particularly advantageous for preventing or treating pathological disorders or esthetic defects of the skin and/or its integuments involving an imbalance in epidermal cell differentiation and/or proliferation.

The invention claimed is:

1. A process for treating an individual with an esthetic defect of the skin, wherein said defect is at least one selected from the group consisting of signs of aging of the skin, a disorder of the epidermal barrier function, a skin desquamation disorder, a cicatrization and/or re-epithelialization defect, the process comprising:
   administering to said individual an active agent comprising a compound that modulates the interaction between a first and a second partner protein, homologs, mutants or fragments of said proteins, wherein said first and second proteins are SASPase and filaggrin-2, or FLG2, and said compound is represented by formula (Ia) or (Ib):

Ia

[Structure of formula Ia showing indeno-pyrimidine scaffold with R1, R2, R3-R7 substituents and two CH3 groups]

Ib

[Structure of formula Ib showing related scaffold with R2, R3-R7 substituents and two CH3 groups]

wherein:
- R¹ is H, a linear or branched, saturated or unsaturated $C_1$-$C_4$ alkyl, or —C(O) R8, wherein $R^8$ is a linear or branched, saturated or unsaturated $C_1$-$C_4$ alkyl;
- R² is =O, —OR⁹ or —OC(O) R9, wherein $R^9$ is H or a saturated $C_1$-$C_2$ alkyl;
- R³, R⁴, R⁵, R⁶, and R⁷ are each independently of each other H; —NO₂; —OH; a fluorine; —CF₃; a linear or branched, saturated or unsaturated $C_1$-$C_4$ alkyl; a phenyl; —OC(O)—CH(Ph)₂; —O-Ph-X wherein X is H, —OH, —NO₂, a fluorine, a linear or branched, saturated or unsaturated $C_1$-$C_4$ alkyl or alkoxy; —O—S(O₂)-Ph-Z wherein Z is a linear or branched, saturated or unsaturated $C_1$-$C_4$ alkyl; —R⁸OH; —OR⁹; —OC(O)R⁹, wherein $R^8$ is a linear or branched, saturated or unsaturated $C_1$-$C_4$ alkyl and $R^9$ is H or a saturated $C_1$-$C_2$ alkyl; —R¹⁰Ph, wherein $R^{10}$ is a linear or branched, saturated or unsaturated $C_1$-$C_4$ alkylene; or —OC(O)—$Y_n$—$Ar_1$—$(X)_m$, wherein
- n is 0 or 1 and m is an integer ranging from 0 to 4, with the proviso that n and m are not simultaneously 0,
- Y is a linear or branched, saturated or unsaturated $C_1$-$C_4$ alkylene,
- X is H, —OH, —NO₂, a fluorine, a linear or branched, saturated or unsaturated $C_1$-$C_4$ alkyl or alkoxy, and
- Ar₁ is

[Two structures: a phenyl ring with @ and * bonds; and a phthalimide-like group with @ and * bonds]

-continued

[Two structures: a phenothiazine-like tricyclic system with @ and * bonds; and a benzothiophene with @ and * bonds]

wherein * is a bond with Y and @ is a bond with X, and physiologically acceptable salts thereof.

2. The process of claim 1, wherein R¹ is H, a methyl, an ethyl, a propyl, or —C(O) R8, wherein $R^8$ is a methyl, an ethyl, or a propyl.

3. The process of claim 1, wherein R² is =O or —OR⁹.

4. The process of claim 1, wherein R³, R⁴, R⁵, R⁶, and R⁷ are each independently of each other H; —OH; a fluorine; a methyl or an ethyl; a phenyl; —OC(O)—CH(Ph)₂; —O-Ph-X, wherein X is H, —OH, a fluorine, a methyl, an ethyl, a methoxy, or an ethoxy; —O—S(O₂)-Ph-Z, wherein Z is a methyl or an ethyl; —R⁸OH; —OR⁹; —OC(O)R⁹, wherein $R^8$ is a methyl or an ethyl and $R^9$ is H or a methyl; —R¹⁰Ph, wherein $R^{10}$ is a methylene or an ethylene, or —OC(O)—$Y_n$—$Ar_1$—$(X)_m$.

5. The process of claim 1, wherein not more than one from among R³, R⁴, R⁵, R⁶, and R⁷ is a —OC(O)—$Y_n$—$Ar_1$—$X_m$.

6. The process of claim 1, wherein n is equal to 0, m is equal to 1, X is a methyl or a methoxy, and Ar₁ is:

[Phenyl ring with @ and * bonds]

wherein * is a bond with Y and @ is a bond with X.

7. The process of claim 1, wherein R³, R⁵, R⁷ and R⁴ or R⁶ are each independently of each other H; —NO₂; —OH; a fluorine; a methyl or an ethyl; a phenyl; —R⁸OH; —OR⁹; —OC(O) R9, wherein $R^8$ is a methyl or an ethyl and $R^9$ is H or a methyl; —R¹⁰Ph, wherein $R^{16}$ is a methylene or an ethylene.

8. The process of claim 1, wherein said compound is represented by formula (II):

(II)

[Structure of formula II: indeno-pyrimidinedione with NH, N-CH3, N-CH3, and a phenyl substituent bearing an ester linkage to a para-methylbenzoate]

* * * * *